(12) United States Patent
Lowe et al.

(10) Patent No.: US 10,383,873 B2
(45) Date of Patent: Aug. 20, 2019

(54) METHOD AND KITS FOR IDENTIFYING OF CDK9 INHIBITORS FOR THE TREATMENT OF CANCER

(71) Applicants: Memorial Sloan-Kettering Cancer Center, New York City, NY (US); St. Jude Children's Research Hospital, Memphis, TN (US)

(72) Inventors: Scott William Lowe, New York City, NY (US); Charles J. Sherr, Memphis, TN (US); Chun-Hao Huang, New York City, NY (US); Amaia Lujambio, New York City, NY (US)

(73) Assignees: MEMORIAL SLOAN-KETTERING CANCER CENTER, New York, NY (US); ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 0 days.

(21) Appl. No.: 15/301,683

(22) PCT Filed: Apr. 2, 2015

(86) PCT No.: PCT/US2015/024057
§ 371 (c)(1),
(2) Date: Oct. 3, 2016

(87) PCT Pub. No.: WO2015/153870
PCT Pub. Date: Oct. 8, 2015

(65) Prior Publication Data
US 2017/0173021 A1 Jun. 22, 2017

Related U.S. Application Data

(60) Provisional application No. 61/975,401, filed on Apr. 4, 2014.

(51) Int. Cl.
| | | |
|---|---|---|
| C12Q 1/68 | (2018.01) |
| A61K 31/519 | (2006.01) |
| A61K 31/445 | (2006.01) |
| G01N 33/574 | (2006.01) |
| C12N 15/113 | (2010.01) |
| A61K 45/06 | (2006.01) |
| A61K 31/40 | (2006.01) |
| A61K 31/404 | (2006.01) |
| A61K 31/44 | (2006.01) |
| A61K 31/4545 | (2006.01) |
| A61K 31/4745 | (2006.01) |
| A61K 31/655 | (2006.01) |
| A61K 31/7048 | (2006.01) |
| A61K 31/7068 | (2006.01) |
| C12Q 1/6886 | (2018.01) |

(52) U.S. Cl.
CPC ............ *A61K 31/519* (2013.01); *A61K 31/40* (2013.01); *A61K 31/404* (2013.01); *A61K 31/44* (2013.01); *A61K 31/445* (2013.01); *A61K 31/4545* (2013.01); *A61K 31/4745* (2013.01); *A61K 31/655* (2013.01); *A61K 31/7048* (2013.01); *A61K 31/7068* (2013.01); *A61K 45/06* (2013.01); *C12N 15/1137* (2013.01); *C12Q 1/6886* (2013.01); *C12Y 207/11022* (2013.01); *C12Y 207/11023* (2013.01); *G01N 33/57423* (2013.01); *G01N 33/57426* (2013.01); *G01N 33/57438* (2013.01); *C12N 2310/531* (2013.01); *C12N 2320/10* (2013.01); *C12N 2320/30* (2013.01); *C12Q 2600/106* (2013.01); *C12Q 2600/158* (2013.01); *G01N 2333/91205* (2013.01); *G01N 2800/52* (2013.01)

(58) Field of Classification Search
None
See application file for complete search history.

(56) References Cited

U.S. PATENT DOCUMENTS

| | | |
|---|---|---|
| 2012/0302629 A1 | 11/2012 | Wang et al. |
| 2013/0053415 A1 | 2/2013 | Rahl et al. |
| 2013/0079345 A1 | 3/2013 | Eickhoff et al. |

OTHER PUBLICATIONS

Sengupta et al (Breast Cancer Research and Treatment, 2014. vol. 143: pp. 113-124).*
Sengupta et al., "Cyclin dependent kinase-9 mediated transcriptional de-regulation of cMYC as a critical determinant of endocrine-therapy resistance in breast cancers", Breast Cancer Res Treat. Jan. 2014, vol. 143(1 ), p. 113-24. Abstract only.
Mitani et al., "Analysis of c-myc DNA amplification in non-small cell lung carcinoma in comparison with small cell lung carcinoma using polymerase chain reaction", Clin Exp Med. 2001, vol. 1 (2), p. 105-11. Abstract only.
Huang et al., "CDK9-mediated transcription elongation is required MYC addication in hepatocellular carcinoma", Genes Dev. Aug. 2014 vol. 28(16), p. 1800-14.

(Continued)

*Primary Examiner* — Celine X Qian
(74) *Attorney, Agent, or Firm* — Hunton Andrews Kurth LLP

(57) ABSTRACT

A method of determining sensitivity to cancer treatment includes the step of determining the presence of overexpression of MYC in a biological sample from a patient suffering from cancer, wherein the presence of overexpression of MYC indicates a sensitivity to a treatment by a CDK9 inhibitor and wherein the cancer is selected from the group consisting of carcinoma, leukemia, and lymphoma.

6 Claims, 40 Drawing Sheets

(56) References Cited

OTHER PUBLICATIONS

International Search Report and Written Opinion of International Application No. PCT/US2015/024057 dated Aug. 17, 2015.
Communication pursuant to Article 94(3) EPC dated Jan. 18, 2019 based on European Patent Application No. 15773170.4.
Haider, C. et al., "Novel Inhibitors of Cyclin-Dependent Kinases Combat Hepatocellular Carcinoma without Inducing Chemoresistance," Molecular Cancer Therapeutics, vol. 12, No. 10, pp. 1947-1957, Oct. 1, 2013.
Zuber, Johannes et al., "RNAi Screen Identifies Brd4 as a Therapeutic Target in Acute Myeloid Leukaemia," Nature, vol. 478, pp. 524-528, 2011.
Zuber, Johannes et al., "An Integrated Approach to Dissecting Oncogene Addiction Implicates a Myb-Coordinated Self-Renewal Program as Essential for Leukemia Maintenance," Genes & Development, vol. 25, pp. 1628-1640, 2011.
Xue, Wen t al., "Senescence and Tumour Clearance is Triggered by p53 Restoration in Murine Liver Carcinomas," Nature, vol. 445, pp. 656-660, 2007.
Tschaharganeh, Darjus et al., "p53-Dependent Nestin Regulation Links Tumor Suppression to Cellular Plasticity in Liver Cancer," Cell, vol. 158, pp. 579-592, Jul. 31, 2014.
Taylor, James et al., "Using Galaxy to Perform Large-Scale Interactive Data Analysis," Current Protocols in Bioinformatics, pp. 10.5-10.5.25, Sep. 2007.
Saborowski, Anna et al., "Mouse Model of Intrahepatic Cholangiocarcinoma Validates FIG-ROS as a Potent Fusion Oncogene and Therapeutic Target," PNAS, vol. 110, No. 48, pp. 19513-19518, Nov. 26, 2013.
Hemann, Michael T. et al., "An Epi-Allelic Series of p53 Hypomorphs Created by Stable RNAi Produces Distinct Tumor Phenoypes in Vivo," Nature Genetics, vol. 33, pp. 396-400, Mar. 2003.
Fellmann, Christof et al., "An Optimized microRNA Backbone for Effective Single-Copy RNAi," Cell Reports, vol. 5, pp. 1704-1713, Dec. 26, 2013.
Zuber, Johannes et al., "Toolkit for Evaluating Genes Required for Proliferation and Survival using Tetracycline-Regulated RNAi," Nature Biotechnology, vol. 29, No. 1, pp. 79-83, Jan. 2011.

Communication Pursuant to Article 94(3) EPC dated Jul. 30, 2018 issued for European Patent Application No. 15773170.4.
Huang, Chun-Hao et al., "Supplemental Material: CDK9-Medicated Transcription Elongation is Required for MYC Addiction in Hepatocellular Carcinoma," Genes & Development, [Retrived from the Internet] http://genesdev.cshlp.org.content/suppl/2014/08/15/28.16.1800.DC1/Supplemental_Figures_Legends.pdf, pp. 1-19, Aug. 15, 2014.
Extended European Search Report dated Sep. 18, 2017 issued for European patent application No. 15773170.4.
Horiuchi, Dai et al., "MYC Pathway Activation in Triple-Negative Breast Cancer is Synthetic Lethal with CDK Inhibition," The Journal of Experimental Medicine, vol. 209, No. 4, pp. 679-696, Mar. 19, 2012.
Cho, Seung-Ju et al., "Ibulocydine is a Novel Prodrug Cdk Inhibitor that Effectively Induces Apoptosis in Hepatocelluar Carcinoma Cells," Journal of Biological Chemistry, vol. 286, No. 22, pp. 19662-19671, Jun. 3, 2011.
Shapiro, Geoffrey I. et al., "Flavopiridol Induces Cell Cycle Arrest and p53-Independent Apoptosis in Non-Small Cell Lung Cancer Cell Lines," vol. 5, pp. 2925-2938, Oct. 1999.
Yin, Tinggui et al., "A Novel CDK9 Inhibitor Shows Potent Antitumor Efficacy in Preclinical Hematologic Tumor Models," Molecular Cancer Therapeutics, vol. 13, No. 6, pp. 1442-1456, Mar. 31, 2014.
Bose, Prithviraj et al., "Cyclin-Dependent Kinase Inhibitor Therapy for Hematologic Maligancies," Expert Opinion on Investigational Drugs, vol. 22, No. 6., pp. 723-738, May 6, 2013.
Cowling, Victoria H. et al., "The MYC Transactivation Domain Promotes Global Phosphorylation of the RNA Polymerase II Carboxy-Terminal Domain Independently of Direct DNA Binding," Molecular and Cellular Biology, vol. 27, No. 6, pp. 2059-2073, Mar. 15, 2007.
Lin, Che-Pin et al., "Targeting c-Myc as a Novel Approach for Hepatocelluar Carcinoma," World Journal of Hepatology, vol. 2, No. 1, pp. 16-20, Jan. 1, 2010.
Holland, Jason P. et al., "89Zr-DFO-J591 for ImmunoPET of Prostate-Specific Membrane Antigen Expression in Vivo," Journal Nucl. Med., vol. 51, pp. 1293-1300, 2010.

\* cited by examiner

| CELL LINE | IC50 (mM) |
|---|---|
| SNU398 | 0.71 |
| HepG2 | 1.05 |
| Huh1 | 1.16 |
| Hep3B | 1.40 |
| SKHep1 | 2.10 |
| SNU475 | 2.83 |
| SNU387 | 3.12 |
| ALEXANDER | 5.30 |
| Li7 | 25.50 |
| JHH2 | 33.87 |
| IMR90 | 3.7 |
| BJ | 3.85 |

*FIG. 3C*

METHOD AND KITS FOR IDENTIFYING OF CDK9 INHIBITORS FOR THE TREATMENT OF CANCER

The present application is a National Stage Application of PCT/US2015/024057, filed Apr. 2, 2015 which claims the priority of U.S. Provisional Application Ser. No. 61/975,401, filed on Apr. 4, 2014. The entirety of the aforementioned applications is incorporated herein by reference.

STATEMENT REGARDING FEDERALLY SPONSORED RESEARCH

This invention was made with government support under CA013106 awarded by the National Institutes of Health. The government has certain rights in the invention.

FIELD

The present application generally relates to methods of treatment for cancer using CDK9 inhibitors and the detection of biomarkers relating to drug-resistant tumors.

BACKGROUND

Hepatocellular carcinoma (HCC) is the third leading cause of cancer-related mortality worldwide. A major risk factor for HCC, the most common type of primary liver cancer, is cirrhosis, frequently caused by chronic viral hepatitis, alcohol abuse, and nonalcoholic fatty liver disease. Although treatment of HCC has greatly improved over the last decades, most HCC patients diagnosed at advanced stages are ineligible for curative ablative therapies such as liver resection or transplantation. The use of the multikinase inhibitor sorafenib in patients with advanced HCC suggests that targeted therapies could be beneficial in this cancer; however, this regimen only extends life expectancy from 8 to 11 months, highlighting the urgent need for new therapeutic approaches.

Recent developments in gene-expression profiling technologies have enabled the molecular classification of HCCs into defined subclasses, creating a solid foundation on which to build more informative clinical trials. Furthermore, exhaustive genomic studies have identified MYC genomic amplifications, β-catenin mutations, and tumor suppressor TP53 inactivation as frequent events in HCC. However, unlike other tumor types, which present genetic drivers that can be therapeutically exploited, such as EGFR mutations in lung cancer and BRAF mutations in melanoma, HCC is genetically heterogeneous and lacks clearly targetable genetic drivers. Thus, it seems likely that more insights into the function of currently "undruggable" genetic lesions will be necessary to develop rational therapies for this disease.

SUMMARY

One aspect of the present application relates to a method of determining sensitivity to cancer treatment in a patient suffering from cancer. The method comprises the steps of: determining the presence of overexpression of MYC in a biological sample from the patient, wherein the presence of overexpression of MYC indicates a sensitivity to a treatment by a CDK9 inhibitor, wherein the cancer is selected from the group consisting of carcinoma, leukemia, and lymphoma.

Another aspect of the present application relates to a method of treating a patient suffering from cancer. The method comprises the steps of: determining the overexpression of MYC in a biological sample from the patient; and administering to the patient an effective amount of a CDK9 inhibitor, if overexpression of MYC is present in the biological sample, wherein the cancer is selected from the group consisting of carcinoma, leukemia, and lymphoma.

Another aspect of the present application relates to a method of evaluating the efficacy of administering CDK9 inhibitors in a patient suffering from cancer. The method comprises the steps of: determining the presence in a biological sample from the patient of suppressed levels of phosphorylation of Ser2 on the C-terminal repeat domain (CTD) of RNA Pol II, where the presence of suppressed levels of phosphorylation of Ser2 in the CTD of RNA Pol II is indicative that CDK9 is being inhibited in the patient, wherein the cancer is selected from the group consisting of carcinoma, leukemia and lymphoma.

Another aspect of the present application relates to a kit for evaluating the efficacy of administering CDK9 inhibitors in a patient suffering from cancer. The kit comprises one or more reagents for determining a level of phosphorylation of Ser2 on the C-terminal repeat domain (CTD) of RNA Pol II in a biological sample from the patient, one or more reagents for processing the biological sample to obtain proteins from the sample, wherein the cancer is selected from the group consisting of carcinoma, leukemia and lymphoma.

Another aspect of the present application relates to a kit for determining the sensitivity to a CDK9 inhibitor in a cancer patient. The kit comprises (1) one or more synthetic oligonucleotides that specifically hybridizes to a human MYC RNA or (2) one or more antibodies that specifically bind to a human MYC protein; and one or more reagents for processing a biological sample to obtain nucleotide molecules or proteins, wherein the patient is suffering from a carcinoma, leukemia or lymphoma.

BRIEF DESCRIPTION OF DRAWINGS

FIG. 1 shows RNAi screen for genes encoding known drug targets.

FIG. 2 shows that CDK9 is required for the proliferation of some HCC cell lines.

FIG. 3 shows pharmacological inhibition of CDK9 in HCC cell lines. (FIG. 3C) Summary of PHA-767491 IC50 values of human cell lines in FIG. 3A.

FIG. 4 shows that MYC expression predicts response to CDK9 inhibition.

FIG. 5 shows that CDK9 mediates transcription elongation of MYC targets in MYC-overexpressing cancer cells.

FIG. 6 shows that transcription elongation is required to maintain proliferation in MYC-overexpressing HCC.

FIG. 7 shows that CDK9 is required for initiation and maintenance of MYC-overexpressing liver tumors. CDK9 is required for initiation and maintenance of MYC-overexpressing liver tumors.

FIG. 8 shows liver regeneration to reveal the therapeutic index associated with CDK9 inhibition in vivo.

FIG. 9 shows inducible and reversible transgenic RNAi mice to reveal the therapeutic index associated with CDK9 inhibition in vivo.

DETAILED DESCRIPTION

Figure 1B:
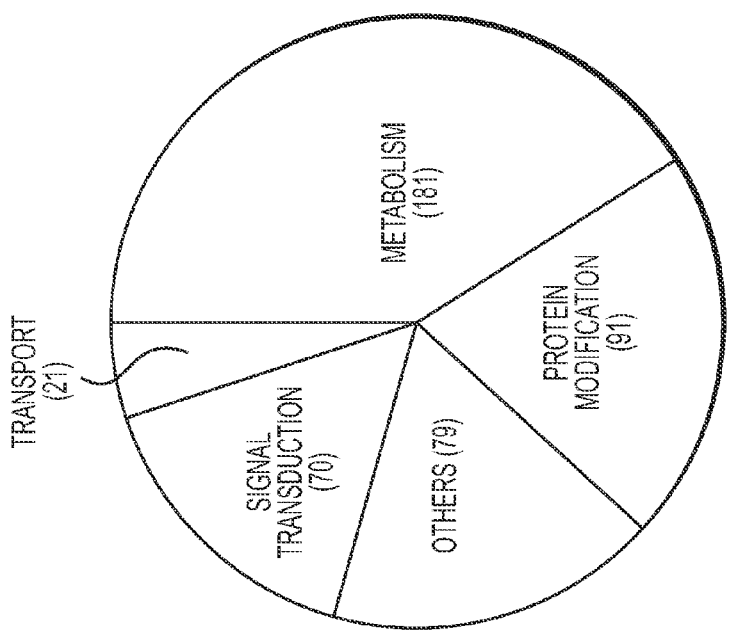
(FIG. 1B) Pathway categories of "drug target" genes included in the library. Numbers indicate the number of genes in each category.

The following detailed description is presented to enable any person skilled in the art to use the present methods and kits. For purposes of explanation, specific nomenclature is set forth to provide a thorough understanding of the present methods and kits. However, it will be apparent to one skilled in the art that these specific details are not required to practice the use of the methods and kits. Descriptions of specific applications are provided only as representative examples. The present methods and kits are not intended to be limited to the embodiments shown, but is to be accorded the widest possible scope consistent with the principles and features disclosed herein.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

As used herein the term "cancer" refers to any of the various malignant neoplasms characterized by the proliferation of cells that have the capability to invade surrounding tissue and/or metastasize to new colonization sites, including but not limited to carcinomas, leukemia, lymphoma, sarcomas, melanoma and germ cell tumors.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which arises from transformed cells of mesenchymal origin. Sarcomas are malignant tumors of the connective tissue and are generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

The term "effective amount" as used herein, refers to an amount sufficient to achieve a desired or intended effect.

Method for Determining Sensitivity to Treatment

MYC gene (c-Myc) is a regulator gene that codes for a transcription factor. The protein encoded by this gene is a multifunctional, nuclear phosphoprotein that plays a role in cell cycle progression, apoptosis and cellular transformation. MYC overexpression induces aberrant proliferation by affecting different biological processes, including gene transcription, protein translation, and DNA replication. Sustained MYC activation in mice creates a state of oncogene addiction while MYC withdrawal in established tumors, including liver carcinomas, leads to tumor involution. Additionally, owing to its role in mediating oncogenic signals, MYC is required for the maintenance of some tumors in which it is not amplified, including murine lung adenomas driven by KRAS and leukemia driven by MLL-AF9. Despite the extensive validation of MYC as a therapeutic target, small molecule MYC antagonists are not available. In principle, the identification of critical molecules and processes required for MYC action in cancer provides an alternative strategy for targeting MYC-driven tumors.

One aspect of the present application relates to a method of determining sensitivity to cancer treatment in a patient suffering from cancer, the method comprising the steps of determining the presence in a biological sample from the patient of over-expression of MYC in tumor tissue, wherein the presence of over-expression of MYC indicates a sensitivity to treatment by a CDK9 inhibitor.

In some embodiments, the cancer is carcinoma, sarcoma, melanoma or germ cell tumor. In other embodiments, the cancer is carcinoma. In some embodiments, the cancer is selected from the group consisting of liver cancer, lung adenocarcinoma, lymphoma, leukemia, bladder cancer, gastric cancer, prostate cancer, colorectal cancer, cutaneous melanoma, head and neck cancer, low-grade glioma, cervical cancer, ovarian cancer, renal cancer and breast cancer. In other embodiments, the cancer is bladder cancer. In other embodiments, the cancer is hepatocellular carcinoma. In yet other embodiments, the cancer is lymphoma, leukemia or non-small cell lung carcinoma (NSCLC).

The biological sample can be a tissue sample, a biopsy sample or a blood sample. The term "over-expression of MYC" refers to a level of MYC expression that is significantly higher than the level of MYC expression in a control sample or a reference value. In some embodiments, "over-expression" refers to a level of expression that is significantly higher than (1) the level of expression in a control sample or (2) a reference value. In some embodiments, "over-expression" refers to a level of expression that is at least 20%, 50%, 100%, 150%, 200%, 300%, 400% or 500% higher than the level of expression in a control sample or a reference value. The level of MYC expression may be determined at transcriptional level (e.g., by determining the level of MYC RNA), at translational level (e.g., by determining the level of MYC protein), or at functional level (e.g., by determining the level of MYC activity).

Overexpression of MYC in tumor tissue samples can be determined with methods well known in the art. All techniques that are presently known, or which may be subsequently discovered, for the evaluation of overexpression of a gene are contemplated for use with the present application. Techniques for evaluating the presence of overexpression of MYC in biological samples include microarray analysis, differential display, PCR, RT-PCR, Q-RT-PCR, Northern blots, Western blots, and Southern blots.

In some embodiments, antibodies are raised against the expressed proteins of MYC in tumors and used to detect the presence of mutations in such tumors by known techniques, such as enzyme-linked immunosorbant assay (ELISA).

In certain embodiments primers are used to support sequencing of nucleotides extracted from a tumor tissue sample. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription.

It is understood that in certain embodiments the primers can also be extended using non-enzymatic techniques, where for example, the nucleotides or oligonucleotides used to extend the primer are modified such that they will chemically react to extend the primer in a sequence specific manner. In other embodiments primers can be extended using isothermal techniques. In some embodiments, techniques and conditions are optimized for the amplification of MYC RNA.

The biological samples can be a tissue sample, such as a biopsy sample, body fluid sample, such as blood, lymph fluid, spinal fluid and saliva, or cell sample from the patient. In some embodiments, the biological sample is a biopsy sample collected from a tumor within the patient.

Overexpression of MYC may be identified by standard molecular biological techniques used to detect the presence of specific biomarkers in a biological sample, such as a tumor tissue sample. Techniques include the use of primers, probes or antibodies, which are capable of interacting with the known RNA or protein sequence of MYC.

In some embodiments, the overexpression of MYC determination is performed on biopsies that are embedded in paraffin wax. Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. The use of FFPE specimens provides a means to improve current diagnostics by accurately identifying the major histological types, even from small biopsies. Since FFPE sample collection and storage is a routine practice in pathology laboratories, this approach allows analysis of overexpression of genes in archived tissues to retrospectively determine sensitivity to CDK9 inhibitors.

As used herein, the term "CDK9 inhibitor" refers to agents that inhibit expression of CDK9 gene or an activity of CDK9 protein. Examples of CDK9 inhibitors include, but are not limited to, PHA 767491, PHA-793887, PHA-848125, BAY 1143572, BAY 1112054, Cdk9 inhibitor II (CAS 140651-18-9 from Calbiochem), DRB, AZD-5438, SNS-032, dinaciclib, LY2857785, flavopiridol, purvalanol B, CDKI-71, CDKI-73, CAN508, FIT-039, CYC065, 3,4-dimethyl-5-[2-(4-piperazin-1-yl-phenylamino)-pyrimidin-4-yl]-3H-thiazol-2-one, wogonin, apigenin, chrysin, luteolin, 4-methyl-5-[2-(3-nitroanilino)pyrimidin-4-yl]-1,3-thiazol-2-amine, shRNAs against CDK9, anti-sense mRNA against CDK9 and anti-CDK9 antibodies.

In some embodiments, biological sample from the patient is a biopsy sample of hepatocellular carcinoma. In some embodiments, the presence of overexpression of the MYC gene in the biopsy sample indicates a sensitivity to the treatment by a CDK9 inhibitor, such as PHA 767491 or an anti-CDK9 shRNA.

In some embodiments, the method further comprises the step of administering to the patient an effective amount of a CDK9 inhibitor, if overexpression of MYC is found in the biological sample.

In some embodiments, the cancer is hepatocellular carcinoma and the absence of overexpression of MYC indicates that the hepatocellular carcinoma is likely to be unresponsive to CDK9 inhibitors. The patient is advised to undergo surgery to remove the hepatocellular carcinoma without accompanying use of therapeutic CDK9 inhibitors. In other embodiments, the cancer is hepatocellular carcinoma and the presence of overexpression of MYC indicates that the hepatocellular carcinoma is likely to be responsive to CDK9 inhibitors. The patient is advised to undergo surgery to remove the hepatocellular carcinoma with administration of CDK9 inhibitors prior to, or after, or both prior to and after, the surgery.

Another aspect of the present application relates to a method of evaluating the efficacy of administering CDK9 inhibitors in a patient suffering from cancer. The method comprises the steps of determining the presence in a biological sample from the patient of suppressed levels of phosphorylation of Ser2 on the C-terminal repeat domain (CTD) of RNA Pol II, wherein the presence of a suppressed level of phosphorylation of Ser2 on the CTD of RNA Pol II is indicative that CDK9 is being inhibited in the patient. As used herein, a "suppressed level of phosphorylation" refers to a level of phosphorylation that is significantly lower than (1) the level of phosphorylation on a control sample or (2) a reference level. In some embodiments, "a suppressed level of phosphorylation" refers to a level of phosphorylation that is about 90%, 80%, 70%, 60%, 50%, 40%, 30%, 20%, 10% or lower than the level of phosphorylation in a control sample or a reference value. The level of phosphorylation of Ser2 on the CTD of RNA Pol II may be determined using methods well known in the art. Techniques for determining the level of phosphorylation of Ser2 on the CTD of RNA Pol II in biological samples include Western blots, Immunohistochemistry (IHC), Immunocytochemistry (ICC), and enzyme-linked immunosorbant assay (ELISA) and Mass spectrometry (MS).

The presence in a biological sample from a patient of suppressed levels of phosphorylation of Ser2 on the CTD of RNA Pol II, may be detected by any of the standard molecular biological techniques used to detect the presence of phosphorylation of an amino acid position, including those listed herein.

If the presence of suppressed levels of phosphorylation of Ser2 on the CTD of RNA Pol II is found within the tumor tissue sample from the patient, greater efficacy may be predicted if a regimen of CDK9 inhibitors is prescribed for the patient. If the presence of a suppressed levels of phosphorylation of Ser2 on the CTD of RNA Pol II is not found within the tumor tissue, then a CDK9 inhibitor is not efficacious.

Method for Treating Cancer

Another aspect of the application relates to a method of treating a patient suffering from cancer. The method comprising the steps of determining the presence in a biological sample from the patient of overexpression of MYC associated sensitivity to administration of a CDK9 inhibitor, and administering an effective amount of a CDK9 inhibitor to the patient if overexpression of MYC is detected in the sample.

In some embodiments, the cancer is carcinoma, sarcoma, melanoma or germ cell tumor. In other embodiments, the cancer is carcinoma. In some embodiments, the cancer is selected from the group consisting of carcinomas, lymphomas and leukemia. In other embodiments, the cancer is hepatocellular carcinoma. In yet other embodiments, the cancer is lymphoma, leukemia or NSCLC.

In some embodiments, an effective amount of one or more CDK9 inhibitors is administered. Each CDK9 inhibitor may be administered at a dose of 0.05-500 mg/m$^2$ per cycle, 0.05-0.2 mg/m$^2$ per cycle, 0.05-0.5 mg/m$^2$ per cycle, 0.05-2 mg/m$^2$ per cycle, 0.05-5 mg/m$^2$ per cycle, 0.05-20 mg/m$^2$ per cycle, 0.05-50 mg/m$^2$ per cycle, 0.05-100 mg/m$^2$ per cycle, 0.05-200 mg/m$^2$ per cycle, 0.2-0.5 mg/m$^2$ per cycle, 0.2-2 mg/m$^2$ per cycle, 0.2-5 mg/m$^2$ per cycle, 0.2-20 mg/m$^2$ per cycle, 0.2-50 mg/m$^2$ per cycle, 0.2-100 mg/m$^2$ per cycle, 0.2-200 mg/m$^2$ per cycle, 0.2-500 mg/m$^2$ per cycle, 0.5-2 mg/m$^2$ per cycle, 0.5-5 mg/m$^2$ per cycle, 0.5-20 mg/m$^2$ per cycle, 0.5-50 mg/m$^2$ per cycle, 0.5-100 mg/m$^2$ per cycle, 0.5-200 mg/m$^2$ per cycle, 0.5-500 mg/m$^2$ per cycle, 2-5 mg/m$^2$ per cycle, 2-20 mg/m$^2$ per cycle, 2-50 mg/m$^2$ per cycle, 2-100 mg/m$^2$ per cycle, 2-200 mg/m$^2$ per cycle, 2-500 mg/m$^2$ per cycle, 5-20 mg/m$^2$ per cycle, 5-50 mg/m$^2$ per cycle, 5-100 mg/m$^2$ per cycle, 5-200 mg/m$^2$ per cycle, 5-500 mg/m$^2$ per cycle, 20-50 mg/m$^2$ per cycle, 20-70 mg/m$^2$ per cycle, 20-100 mg/m$^2$ per cycle, 20-200 mg/m$^2$ per cycle, 20-500 mg/m$^2$ per cycle, 50-70 mg/m$^2$ per cycle, 50-100 mg/m$^2$ per cycle, 50-200 mg/m$^2$ per cycle, 50-500 mg/m$^2$ per cycle, 70-100 mg/m$^2$ per cycle, 70-150 mg/m$^2$ per cycle, 70-200 mg/m$^2$ per cycle, 70-300 mg/m$^2$ per cycle, 70-400 mg/m$^2$ per cycle, 70-500 mg/m$^2$ per cycle, 100-150 mg/m$^2$ per cycle, 100-200 mg/m$^2$ per cycle, 100-300 mg/m$^2$ per cycle, 100-400 mg/m$^2$ per cycle, 100-500 mg/m$^2$ per cycle, 200-300 mg/m$^2$ per cycle, 200-400 mg/m$^2$ per cycle, 200-500 mg/m$^2$ per cycle, 300-400 mg/m$^2$ per cycle, 300-500 mg/m$^2$ per cycle and 400-500 mg/m$^2$ per cycle. In some embodiments, the CDK9 inhibitor is administered at about 10, 20, 30, 40, 50, 60, 70, 80, 90 or 100 mg/m$^2$ per cycle. Each cycle may have a length of 1, 2, 3, 4, 5, 6, 7, 8 9 or 10 days, or 1, 2, 3, 4, 5, 6, 7, 8 or 9 weeks.

The CDK9 inhibitor may be administered parentally, intravenously, intra muscularly, subcutaneously, or orally.

In some embodiments, the CDK9 inhibitor is administered at a dose of 10-100 mg/m$^2$ per cycle, 10-20 mg/m$^2$ per cycle, 20-40 mg/m$^2$ per cycle, 40-60 mg/m$^2$ per cycle, 60-80 mg/m$^2$ per cycle, or 80-100 mg/m$^2$ per cycle The dose range for CDK9 inhibitor administration as part of the methods disclosed herein ranges between 20 mg/m$^2$ to 100 mg/m$^2$ CDK9 inhibitor. In some embodiments, CDK9 inhibitor is given parenterally. In some embodiments, CDK9 inhibitor at the above described dose is given by IV infusion over 3-24 hours. CDK9 inhibitors are commercially available from many sources. The dose to be administered to a subject having a cancer can be determined by a physician based on the subject's age, and physical condition, the sensitivity of the cancer to an antineoplastic agent the nature of the cancer and the stage and aggressiveness of the cancer. The dosage ranges herein are not intended to limit the scope of the invention in any way. In some instances dosage levels below the lower limit of the aforesaid dose range may be more than adequate, while in other cases still larger doses may be employed without causing any harmful side effect.

In other embodiments, a CDK9 inhibitor, is administered in conjunction with surgery that removes the cancer tissue containing an overexpression of MYC. In some embodiments, the CDK9 inhibitor is administered before surgery and after surgery. In other embodiments, the CDK9 inhibitor is administered after surgery.

In some embodiments, a CDK9 inhibitor, is administered before, after or in conjunction with radiation therapy.

In some embodiments, a combination of CDK9 inhibitors and other chemotherapeutic agents, such as taxanes, Teniposide, Gemcitabine, Dacarbazine, Flumequine and anthracyclines is administered.

In some embodiments, a combination of CDK9 inhibitors and other inhibitors, such as Sorafenib, Atorvastatin, tivantinib, sunitinib and Crizotinib is administered.

Kits

Another aspect of the present application relates to a kit for practicing the methods of the application. Kits of the application may supply the means to detect overexpression of MYC in a biological sample obtained from patient who is a candidate for treatment with a CDK9 inhibitor. In some embodiments, the kit is a package or a container comprising one or more reagents for specifically detecting overexpression of MYC in a biological sample. In some embodiments, the one or more reagents comprise two or more nucleotide primers or probes that specifically hybridize to one or more MYC RNA transcripts, or alternatively, antibodies for detection of MYC protein.

In some embodiments, the kit comprises comprise one or more reagents for determining the level of phosphorylation of Ser2 on the CTD of RNA Pol II. The level of phosphorylation of Ser2 on the CTD of RNA Pol II may be determined using methods well known in the art. Techniques for determining the level of phosphorylation of Ser2 on the CTD of RNA Pol II in biological samples include Western blots, Immunohistochemistry (IHC), Immunocytochemistry (ICC), and enzyme-linked immunosorbant assay (ELISA) and Mass spectrometry (MS).

In other embodiments, the kit comprises a package insert describing the kit and methods for its use.

In some embodiments, the kits comprises one or more of the components selected from the group consisting of (1) containers for processing biological samples to obtain nucleotide molecules, in particular RNA, or proteins; (2) reagents for processing biological samples to obtain nucleotide molecules or proteins; (3) RNA purification and filtration components, such as microbeads, or protein purification and filtration components, such as anion exchange columns; (4) reagents for RNA filtration and purification, or protein filtration and purification; (5) primers and/or other synthetic oligonucleotides to be used for molecular biology techniques for nucleotide sequence analysis, including RNA sequencing; (6) microarrays designed for nucleotide or protein sequence analysis, including hybrid capture arrays; (7) reagents for determining the level of phosphorylation of Ser2 on the CTD of RNA Pol II, and (8) means by which nucleotide sequences or antibody binding may be visualized, including software programs.

The foregoing descriptions of specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

EXAMPLES

Example 1

Material and Method

Pooled Negative Selection RNAi Screening

A custom shRNA library focused on 442 drug target genes was designed using miR30-adapted BIOPREDsi predictions (six shRNAs per gene) and constructed by PCR-cloning a pool of oligonucleotides synthesized on 55 k customized arrays (Agilent Technologies) as previously described (Zuber J, McJunkin K, Fellmann C, Dow L E, Taylor M J, Hannon G J, Lowe S W. 2011. Toolkit for evaluating genes required MYC depends on transcription elongation for proliferation and survival using tetracycline-regulated RNAi (Zuber J et al., Nat Biotechnol (2011) 29: 79-83; Zuber J, et al., Nature (2011) 478: 524-528.). The list of genes was obtained from DrugBank (version 2.5; www.drugbank.ca) and was manually curated, excluding ambiguous or redundant targets. After sequence verification, 2245 shRNAs (five to six per gene) were combined with several positive and neutral control shRNAs (n=20) at equal concentrations in one pool.

The library was cloned into TRMPV-Neo and transduced into Tet-on murine HCC MP1 cells using conditions that predominantly lead to a single retroviral integration and represent each shRNA in a calculated number of at least 1000 cells. Transduced cells were selected for 5 d using 1 mg/mL G418 (Invitrogen); at each passage, >20 million cells were maintained to preserve library representation throughout the experiment. After drug selection, T0 samples were obtained (20 million cells per replicate) and sorted for Venus+ cells. After 12 d (six passages, T12), ~20 million shRNA-expressing (dsRed+Venus+) cells were sorted for each replicate using a FACSAriaII (BD Biosciences). Genomic DNA from T0 and T12 samples was isolated by two rounds of phenol extraction using PhaseLock tubes (5 Prime) followed by isopropanol precipitation.

Statistical significance was calculated by two-tailed Student's t-test. Correlation was calculated by Pearson test. Prism 5 software was used to calculate the IC50 values. Significance values are $P<0.05$ (*), $P<0.01$ (), and $P<0.001$ (*).

Total RNA was isolated using RNeasy Mini Kit and RNase-Free DNase Set (Qiagen). Total mRNA was isolated using Oligotex mRNA Mini Kit (Qiagen) following manufacturer's instructions. cDNA synthesis and qRT-PCRs were performed as previously described (Xue W et al., Nature (2007) 445: 656-660.). Quantitative PCR analysis was performed on a ViiA™ 7 (Life Technologies). All signals were quantified using the deltaCt method and were normalized to the levels of GAPDH. Each reaction was done in triplicate using gene-specific primers.

Deep-sequencing template libraries were generated by PCR amplification of shRNA guide strands as previously described (Zuber et al. Genes Dev (2011) 25:1628-1640). Libraries were analysed on an Illumina Genome Analyser at a final concentration of 8 pM; 50 nucleotides of the guide strand were sequenced using a custom primer. To provide a sufficient baseline for detecting shRNA depletion in experimental samples, the experiment aimed to acquire 500 reads per shRNA in the T0 sample, which required more than twenty million reads per sample to compensate for disparities in shRNA representation inherent in the pooled plasmid preparation or introduced by PCR biases. With these conditions, the experiment acquired T0 baselines of >500 reads for 2246 (99.16% of all) shRNAs. Sequence processing was performed using a customized Galaxy platform (Taylor J, Schenck I, Blankenberg D, Nekrutenko A. 2007. Using galaxy to perform large-scale interactive data analyses. Curr Protoc Bioinformatics Chapter 10: Unit 10 15.).

Animal Studies

All mouse experiments were approved by the Memorial Sloan-Kettering Cancer Center (MSKCC) Animal Care and Use Committee (protocol no. 11-06-011). Mice were maintained under specific pathogen-free conditions, and food and water were provided ad libitum. For conditional RNAi experiments in vivo, Tet-on murine HCC MP1 cells were transduced with luciferase-hygro and TRMPV-Neo-miR-E shRNA constructs. One million murine or human HCC cells were ortothopically transplantated into female nude recipient mice (NCR nu/nu, purchased from Charles River laboratories and Harlan Laboratories), as described previously (Saborowski et al. 2013 Proc Natl Acad Sci USA. 2013 Nov. 26; 110(48):19513-8. doi: 10.1073/pnas.1311707110.). For whole-body bioluminescent imaging, mice were intraperitoneally injected with 50 mg/kg D-Luciferin (Goldbio), and after 10 min, analysed using an IVIS Spectrum system (Caliper LifeSciences). Quantification was performed using Living Image software (Caliper LifeSciences) with standardized round regions of interests covering the mouse trunk and extremities. For shRNA induction, animals were treated with doxycycline in drinking water (2 mg/ml with 2% sucrose; Sigma-Aldrich) and food (625 mg/kg, Harlan Laboratories). For PHA-767491 treatment trials, PHA-767491 was solved in ultrapure distilled water, filtered by 0.2 M filters, and diluted to a final concentration of 5 mg/ml. Mice were orally given twice daily PHA-767491 (50 mg/kg) or a similar volume of vehicle (water). The sick animals were sacrificed and liver tumors were used for further analysis. Liver tumors were excised, formalin-fixed and paraffin-embedded, frozen, or embedded in OCT.

To produce Tet-on murine HCC cells, liver progenitor cells from p53Loxp/Loxp mouse were transduced with CreER and Myc-IRES-rtTA3 and then transplanted into recipient mice. After tumor formation, the tumor was established as a cell line and different clones were tested for their ability to induce shRNAs expressed from TRMPV-neo in the presence of doxycycline, and for functionality using neutral (Renilla) and lethal (Rpa3) control shRNAs in competitive proliferation assays. In this assay, shRNA-expressing and non-expressing cells were mixed and tested for their relative proliferation potential. Taking into account the similar behavior of the different clones, Myc;p53−/− clone #1 was selected as the screening cell line (hereafter, referred to as MP1).

The remaining HCC murine cell lines were derived from liver progenitor cells from p53LoxP/LoxP mice: MP-CH stands for Myc;p53−/− (similar to MP1) but was generated from independent infections; Myc-AL was generated by overexpressing Myc cDNA in p53LoxP/LoxP liver progenitor cells although p53 locus is intact; KrasG12D;p53−/− cells were originated by overexpressing mutant Kras and deleting p53.

Plasmids

For conditional RNAi experiments, shRNAs were expressed from the TRMPV-Neo vector from either miR-30 or miR-E backbones, which have been described previously (and are available from Addgene, catalog no. 27990, or on request (e.g. Zuber J, et al. Nat Biotechnol (2011) 29: 79-83;

Fellmann C, et al., Hoffmann T. et al., Cell Rep (2013) 5: 1704-1713.). To produce Tet-on murine HCC MP1 cells, liver progenitor cells from p53Loxp/Loxp mice were transduced with CreER and Myc-IRES-rtTA3.

For MYC rescue experiments, the wild-type human MYC cDNA was subcloned into MSCV-PGK-Puro-IRES-GFP (MSCV-PIG) (Hemann M T, et al., Nat Genet, (2003) 33: 396-400.)

For the in vivo experiments, cancer cells were infected with Luciferase-hygro. Human cell lines were infected with MSCV-RIEP (MSCV-rtTA3-IRES-EcoR-PGK-Puro) (Zuber J, et al. Genes Dev (2011) 25: 1628-1640.). Knockdown efficiency or overexpression was evaluated by immunoblotting. shRNA sequences are available. The pT3 transposon and pT3-EF1a-Myc vectors were a kind gift of Dr. Xin Chen, University of California at San Francisco. To generate the constitutive expression vector pT3-EF1a (Tschaharganeh D F, et al. Cell (2014). July 31; 158(3):579-92. doi: 10.1016/j.cell.2014.05.051.), the CpG-free EF1a promoter from pCpGfree-vitroBmcs (InvivoGen) was inserted into pT3, and a GFP-miR-E fragment was cloned following the EF1a promoter.

Immunoblotting

Liver tissues and cell pellets were lysed in Laemmli buffer or protein lysis buffer (200 mM NaCl, 0.2% NP40, 50 mM Tris at pH 7.5, 1% Tween20, protease and phosphatases inhibitors) using a tissue homogenizer. Equal amounts of protein were separated on 12% SDS-polyacrylamide gels and transferred to PVDF membranes. The abundance of β-actin was monitored to ensure equal loading. Images were analyzed using the AlphaView software (ProteinSimple). Detection in immunoblots was performed using antibodies for CDK9 (Santa Cruz Biotechnology), MCM6 (Santa Cruz Biotechnology), PSMB2 (Santa Cruz Biotechnology), β-Actin (AC-15, Sigma), p53 (Leica Biosystems), MYC (Abcam), CCNT1 (Santa Cruz Biotechnology), phopho-Ser2 RNA Pol II (Cell Signaling), and RNA Pol II (Santa Cruz Biotechnology). For Ki67 staining (VP-K451, Vector Laboratories), organ samples were fixed in fresh 4% paraformaldehyde overnight at 4° C. and further subjected to routine histological procedures for embedding in paraffin. Images were taken on a Zeiss Axio Imager Z2 system.

Proliferation Assays

Competitive proliferation assays using shRNAs in TRMPV-Neo vector (with miR-30 or miR-E backbone) were performed as described previously (Zuber J, et al. Nature (2011) 478: 524-528). Proliferation assays for PHA-767491 were performed in vitro by counting the viable cell numbers over 72 h in the presence of different PHA-767491 concentrations. Dead cells were excluded using propidium iodide (PI) staining to score cells with sub-2N DNA content. Measurements of cell concentration were performed on a Guava Easycyte (Millipore), gating only viable cells (FSC/SSC/PI-). Proliferation rates were calculated by dividing cell concentration at 72 h and cell concentration at 0 h, divided by 72. Relative proliferation rates were calculated by normalizing to the rate of vehicle-treated cells. Population doublings were calculated by calculating log 2 (cells at end point/cells at initial point) divided by time in days.

shRNA Experiments in Human HCC Cell Lines

HepG2, Hep3B, SKHep1, SNU398, SNU475, and Alexander cells were modified to express the ecotropic receptor and rtTA3 by transducing MSCV-RIEP (MSCV-rtTA3-IRES-EcoR-PGK-Puro) followed by drug selection (1 μg/mL puromycin for 1 wk). The resulting cell lines were transduced with ecotropically packaged TRMPV-Neo-shRNA retroviruses with either miR-30 or miR-E backbone, selected with 1 mg/mL G418 for 1 wk, and treated with 1 μg/mL dox to induce shRNA expression. The relative change in Venus+dsRed+ (shRNA+) cells was monitored on a Guava Easycyte (Millipore) by performing proliferation competitive assays.

Deep-sequencing template libraries were generated by PCR amplification of shRNA guide strands as previously described (Zuber J, et al. 2011. Genes Dev 25: 1628-1640.). Libraries were analysed on an Illumina Genome Analyser at a final concentration of 8 pM; 50 nucleotides of the guide strand were sequenced using a custom primer. To provide a sufficient baseline for detecting shRNA depletion in experimental samples, the experiment aimed to acquire 500 reads per shRNA in the T0 sample, which required more than twenty million reads per sample to compensate for disparities in shRNA representation inherent in the pooled plasmid preparation or introduced by PCR biases. With these conditions, the experiment acquired T0 baselines of >500 reads for 2246 (99.16% of all) shRNAs. Sequence processing was performed using a customized Galaxy platform (Taylor J, Schenck I, Blankenberg D, Nekrutenko A. 2007. Using galaxy to perform large-scale interactive data analyses. Curr Protoc Bioinformatics Chapter 10: Unit 10 15.).

Chromatin Immunoprecipitation (ChIP)

ChIP assays were performed as previously described (Bracken A P, et al., Genes Dev (2006) 20: 1123-1136). Briefly, cross-linking was performed with 1% formaldehyde, and cells were lysed in SDS buffer. DNA was fragmented by sonication (Bioruptor). ChIP for RNA Pol II was performed using a specific antibody (N-20, Santa Cruz Biotechnology). DNA enrichment was measured by quantitative PCR performed using SYBR Green (ABI) on a ViiA 7 (Life Technologies). Each reaction was done in triplicate using gene-specific primers. Each immunoprecipitate signal was referenced to an input standard curve dilution series (immunoprecipitate/input) to normalize for differences in starting cell number and for primer amplification efficiency. Pausing index, also known as traveling ratio, was calculated as the ratio between the RNA Pol II bound to the transcription start site and the RNA Pol II bound to the gene body.

Small Animal PET Imaging

For in vivo assays, human holo-Transferrin was labeled with 89Zr. The 89Zr was prepared as previously described (Holland J P, Sheh Y, Lewis J S. 2009. Standardized methods for the production of high specific-activity zirconium-89. Nucl Med Biol 36: 729-739.). Female athymic nude mice were inoculated with 5×106 to 10×106 cells reconstituted in a 1:1 mixture of medium and Matrigel in the shoulder. After tumors reached ~500 mm3, mice were treated with PHA-767491 for 3 d and, 2 d after, injected with 275-300 mCi of 89Zr-holoTransferrin via the tail vein. At various time points following injection (24-48 h), mice were scanned using a MicroPET Focus 120 Scanner (Concorde Microsystems). Approximately 5 min before recording PET images, mice were anesthetized by inhalation of 1%-2% isoflurane (Baxter Healthcare) in an oxygen gas mixture and placed on the scanner bed. Image reconstruction and processing details have been reported elsewhere (Holland J P et al., J Nucl Med (2010) 51: 1293-1300). For biodistribution studies, mice (n=5; 10 tumors) were euthanized by CO2 at 48 h post-injection, and organs were harvested immediately. The radioactivity in each organ was counted alongside a known amount of 89Zr, the counts were correlated to activity, and decay was corrected. The organs were then weighed, and the percentage of the injected dose per gram (% ID/g) in each tissue was calculated.

Hydrodynamic Tail Vein Injection

A sterile 0.9% NaCl solution/plasmid mix was prepared containing 5 µg of DNA of pT3-EF1a-Myc and 20 µg of DNA of pT3-EF1a-GFP-miRe Transposon vector together with CMV-SB13 Transposase (1:5 ratio) for each injection. FVBN mice from JAX were injected with the 0.9% NaCl solution/plasmid mix into the lateral tail vein with a total volume corresponding to 10% of body weight in 5-7 sec.

Example 2

RNAi Screen for Genes Encoding Known Drug Targets

Growth-inhibitory effects of several available CDK9 inhibitors have been compared with the anti-proliferative effects of numerous CDK9 shRNAs and a lead compound identified (PHA-767491, a dual CDC7/CDK9 inhibitor) that most closely recapitulated shRNA-mediated CDK9 inhibition in both human and murine cell lines. While this molecule shows both in vitro and in vivo efficacy, given its extremely simple structure increased potency, selectivity, and pharmacodynamics can be obtained by modifying its scaffold.

In order to get improved CDK9 inhibitors for the clinical management of MYC-overexpressing tumors, PHA-767491 was docked into the existing crystal structure of CDK9 and CDC7 and identified potential regions of the molecule that can be derivatized to improve potency, selectivity, and pharmacodynamics. In this project, a number of these structures are synthesized, utilizing the Organic Synthesis Core Facility at MSKCC or, potentially, Takeda, and in vitro potency and selectivity is tested using well-established kinase assays. The best molecules identified are moved to cell-based validation assays, using Ser2 phosphorylation of RNA Pol II as a biomarker. A panel of murine and human cancer cell lines can be provided, which exhibit differential sensitivity to CDK9 shRNAs, and it is possible to compare the IC50's generated with the above molecules to further confirm compound selectivity. Kinome-wide assays such as KiNativ can be employed to further confirm the specificity of identified compounds in situ. Finally, the best candidates are tested in established in vivo models, and using the Antitumor Assessment core at MSKCC, it is possible to define the pharmacodynamics parameters for these compounds.

The exemplary approaches are based on the finding that PHA-767491 is more selective for CDK9 than other available inhibitors. It is also possible to modify the scaffolds of other previously identified CDK9 inhibitors.

By defining CDK9 inhibition as an "anti-MYC" approach here, it is possible to identify a patient selection criteria (high MYC) and a pharmacodynamics marker (Ser2 phosphorylation of RNA Pol II), which can greatly facilitate preclinical and clinical development of this strategy in both hematological and solid cancers.

To systematically probe candidate drug targets required for HCC maintenance, exemplary embodiment of a screening platform and shRNA library can be provided to facilitate the identification of cancer dependencies in a defined genetic context. For this screening system, the experiment established a murine HCC model driven by Myc overexpression and p53 loss, which mimics two of the most common genetic drivers in human HCC. These cells also expressed a reverse tetracycline transactivator (rtTA) that enabled efficient induction of tet-responsive transgenes introduced by retroviral mediated gene transfer.

Figure 1A:
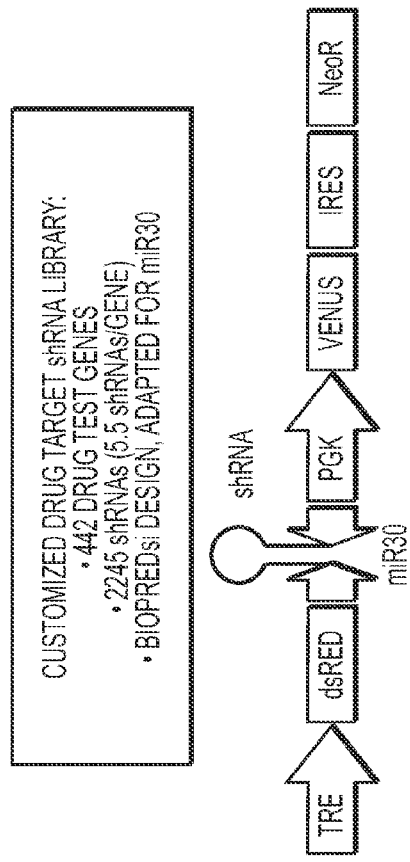
(FIG. 1A) Library features and schematic of the TRMPV-neo vector. TRE, tetracycline regulated element.

To focus on genes whose protein products can be targeted by established agents, the screen used a custom shRNA library against 442 genes encoding known drug targets (~6 shRNAs/gene) (FIG. 1A). This target list consisted of genes involved in metabolism, protein modifications, signal transduction, and macromolecular transport (FIG. 1B), with a bias for receptors and kinases. The shRNAs were cloned downstream of a tetracycline responsive promoter in TRMPV-neo (FIG. 1A), an inducible expression vector that was previously optimized for negative-selection RNAi screens.

Figure 1C:
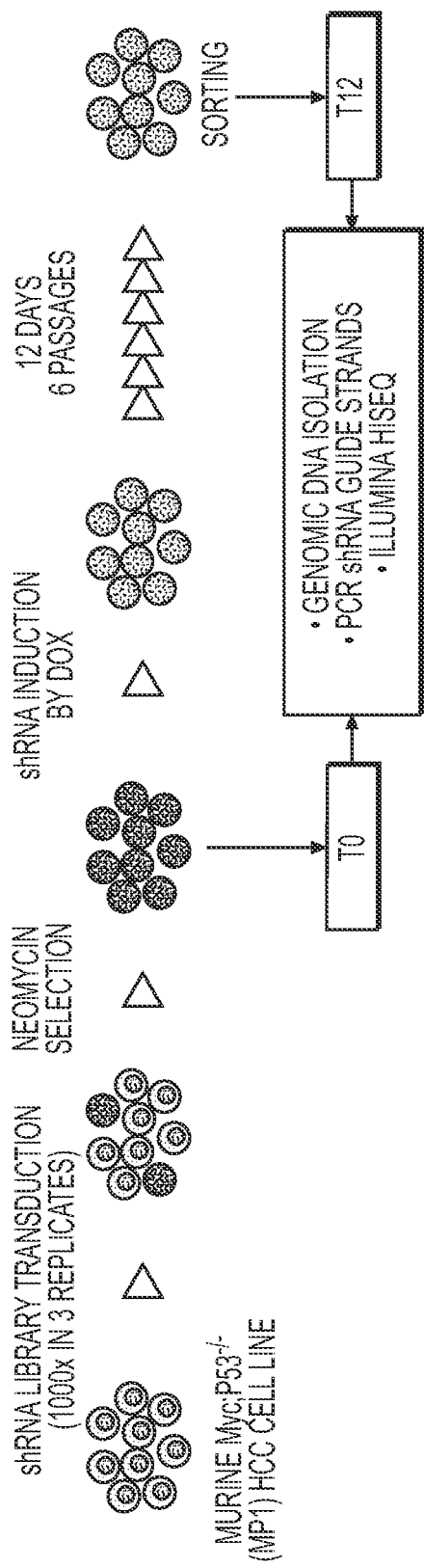
(FIG. 1C) RNAi screening strategy.
Figure 1D:
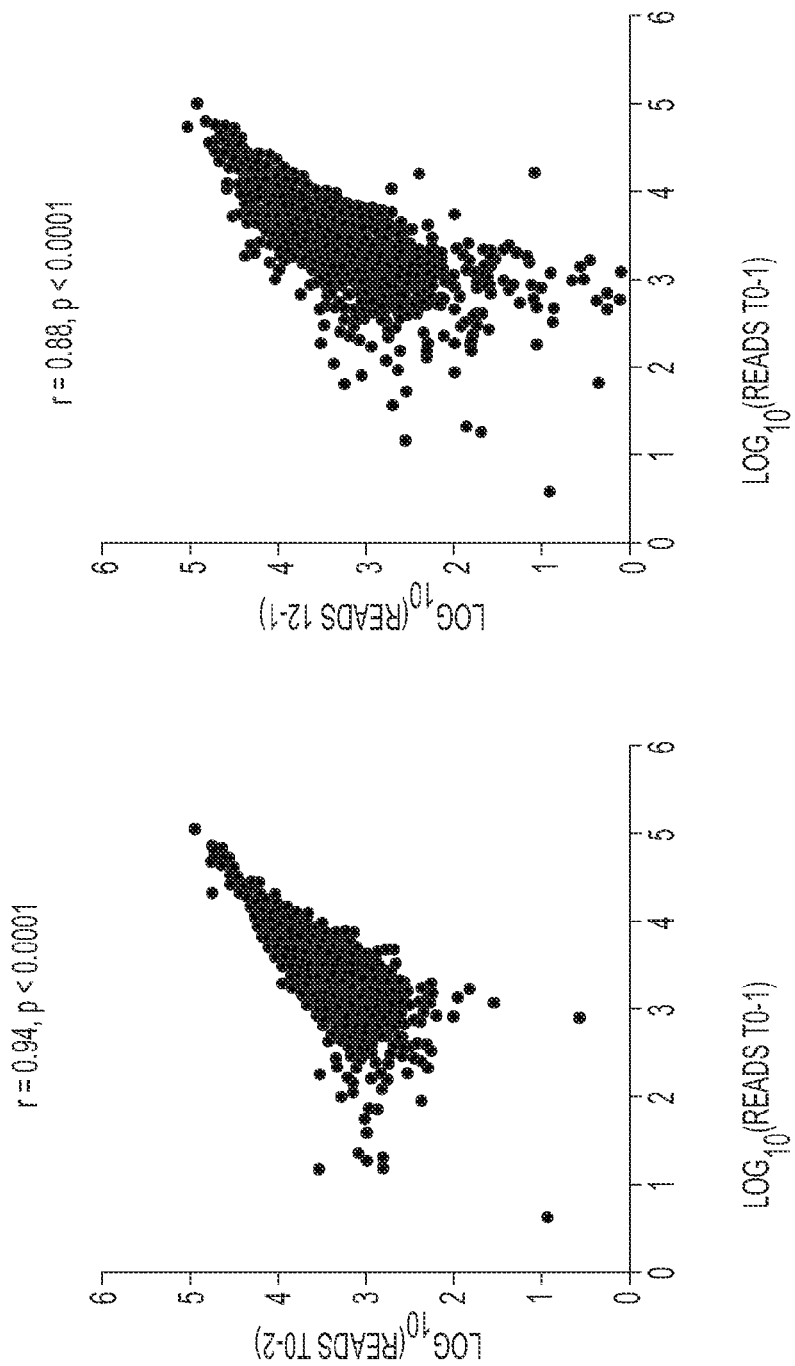
(FIG. 1D) Representative scatter plots illustrating the correlation of normalized reads per shRNA between replicates at the beginning of the experiment (left) and replicates at different time points (right).

The library was transduced as one pool in triplicate into murine Myc;p53−/− HCC cells (hereafter, MP1 cells) at low multiplicity of infection (MOI<1). Transduced cells were cultured such that, in theory, each shRNA was represented in at least 1000 cells throughout the experiment (FIG. 1C). After G418 selection, shRNAs were induced by addition of doxycycline (dox), and changes in shRNA representation after 12 days of culture were quantified using deep sequencing of shRNA guide strands amplified from genomic DNA of sorted shRNA-expressing cells (FIG. 1C). The correlation of normalized shRNA reads present in the replicates at T0 was close to 1 but substantially decreased when comparing T0 and T12 within the same replicate, suggesting changes in library representation associated with shRNA depletion (FIG. 1D).

Figure 1E:
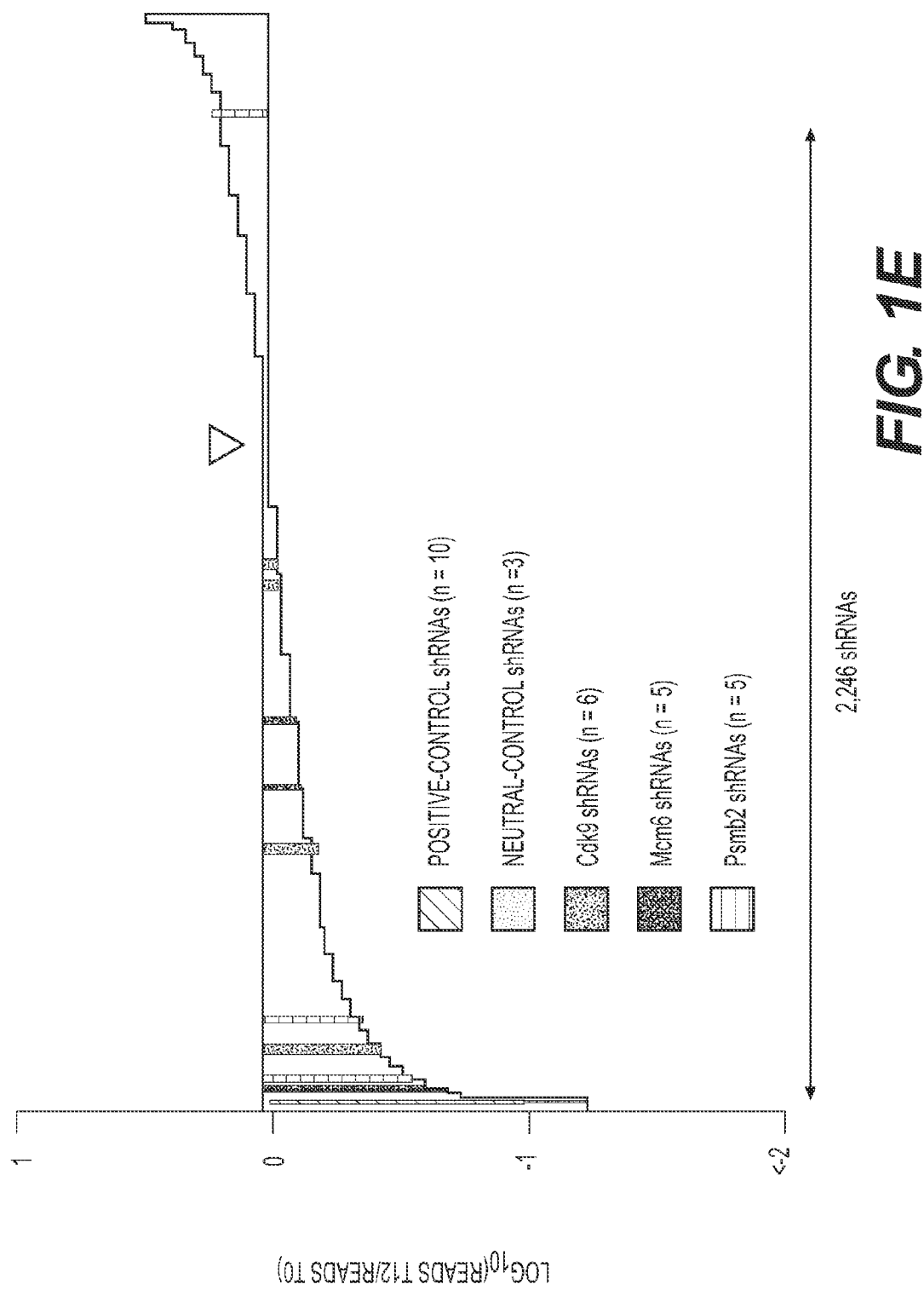
(FIG. 1E) Pooled negative-selection screening results in MP1 murine HCC cells. shRNA abundance ratios of 2046 shRNAs were calculated as the number of normalized reads after 12 days of culture on doxycycline (T12) divided by the number of normalized reads before doxycycline treatment (T0), and plotted as the mean of three replicates in ascending order. MP1, Myc; p53−/− clone 1 murine HCC cells; T0, cell population at the beginning of the experiment; T12, cell population at the end of the experiment, at day 12; dox, doxycycline; r, Pearson correlation coefficient.

Using the scoring criterion of more than 5-fold average depletion in three independent replicates, 43 shRNAs were strongly depleted (FIG. 1E): these included all positive-control shRNAs targeting essential genes (Rpa1, n=1; Rpa3, n=5; Pcna, n=1) as well as three shRNAs targeting Myc—the driving oncogene in this model. For a hit to undergo further analysis, it required that at least two independent shRNAs targeting a particular gene were identified in the primary screen. Genes fulfilling these criteria included the proteasome component Psmb2 (proteasome subunit beta type 2), the replication factor Mcm6 (minichromosome maintenance complex component 6), and the transcription elongation factor CDK9 (cyclin-dependent kinase 9).

Example 3

Competitive Inhibition Assay

Figure 2A:
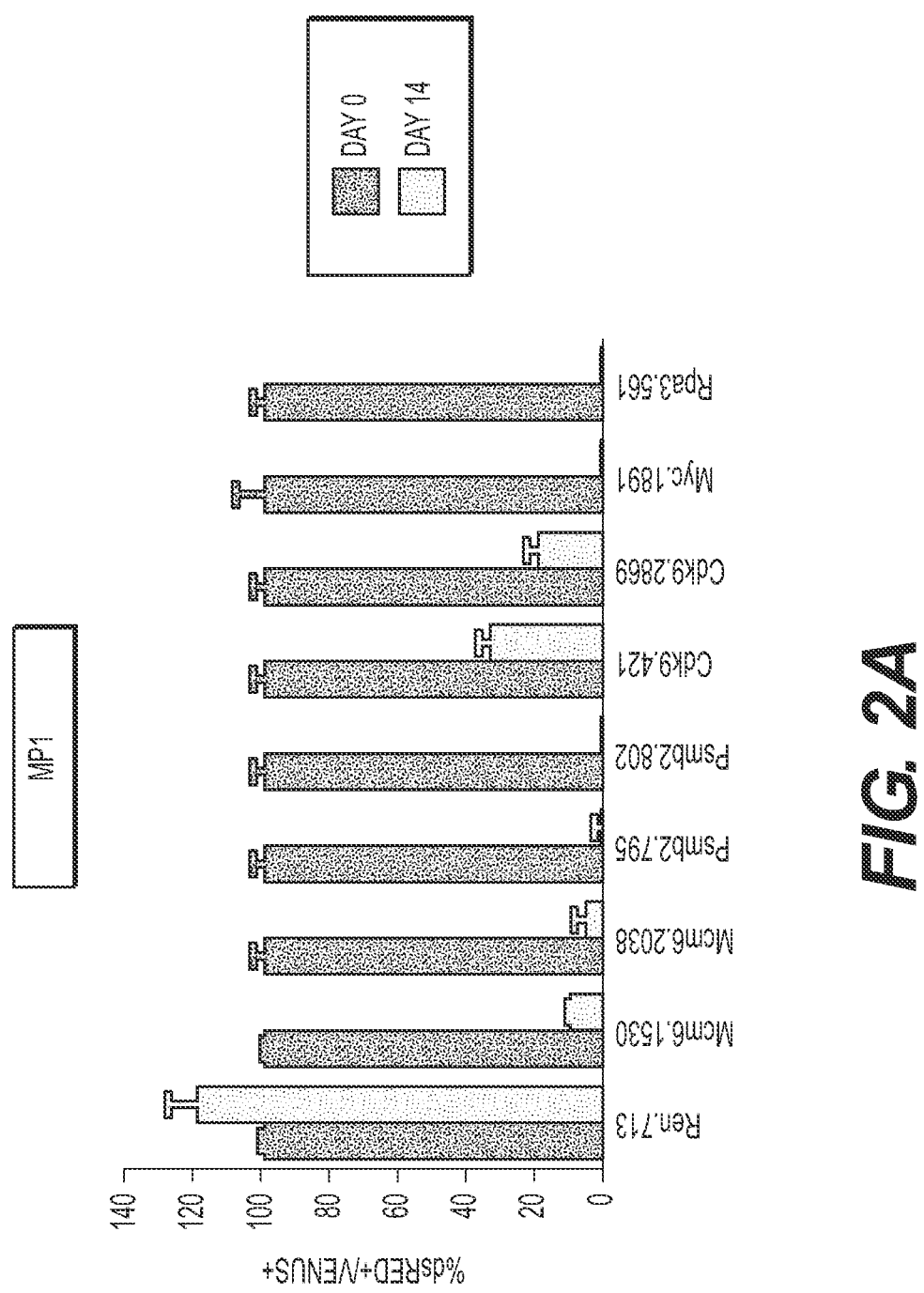
(FIG. 2A) Competitive proliferation assay. G418-selected Venus+ cells were mixed with untransduced cells at 1:1 ratio, and subsequently cultured in the presence of doxycycline. The percentage of Venus$^+$dsRed$^+$ (shRNA-expressing) cells was determined at different time points (results at day 0 and day 14 are shown and are relative to day 0). Changes were used as readout of growth inhibitory effects. Values are mean+SD of three independent replicates. The graphs show the validation of the candidate shRNAs as well as control shRNAs (Ren.713; Myc.1891 and Rpa3.561) in MP1 murine HCC cells.
Figure 2B:
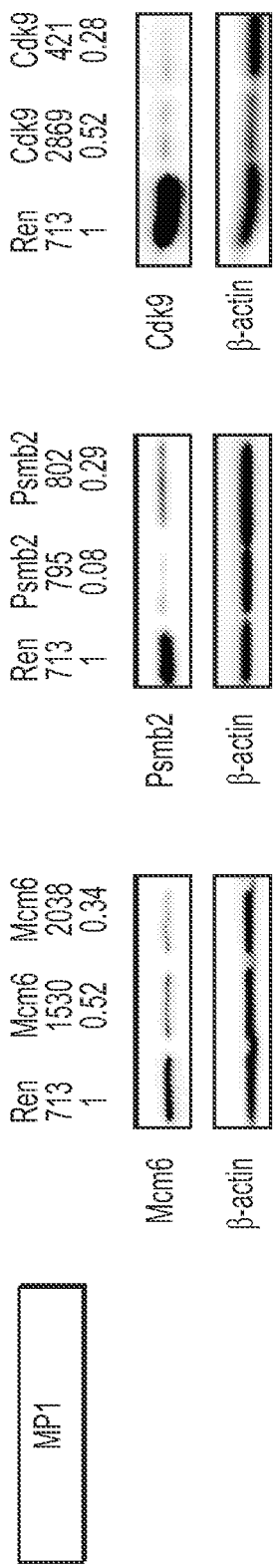
(FIG. 2B) Immunoblots showing the knockdown induced by shRNAs expressed from TRMPV-neo in MP1 murine HCC cells. β-actin was used as loading control.
Figure 2C:
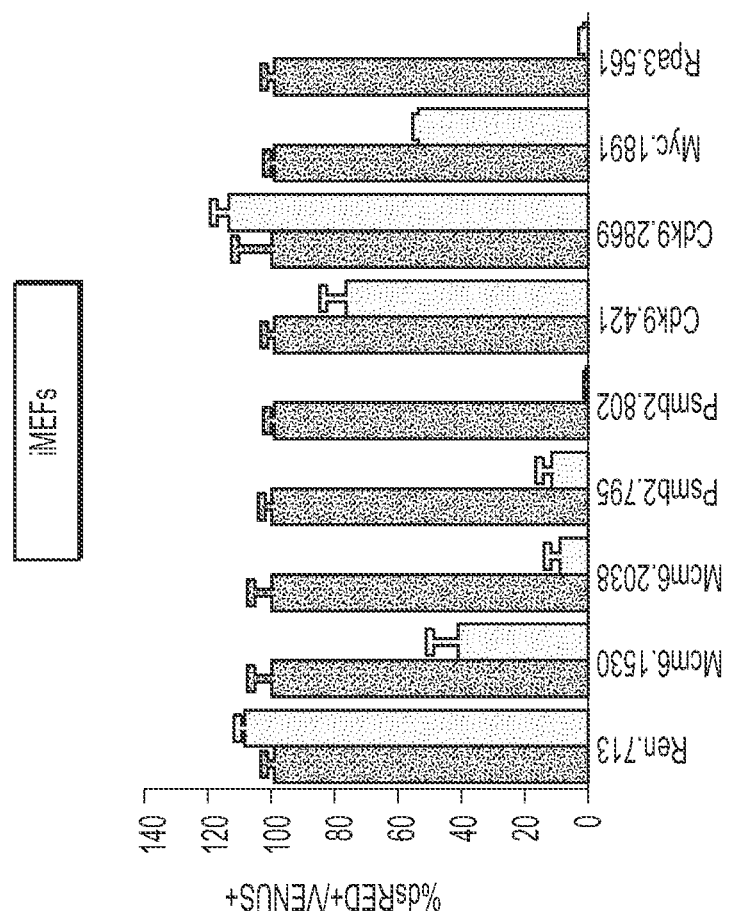
(FIG. 2C) Competitive proliferation assay of control and candidate shRNAs expressed from TRMPV-neo in immortalized MEFS (iMEFs), as described in FIG. 2A.
Figure 2D:
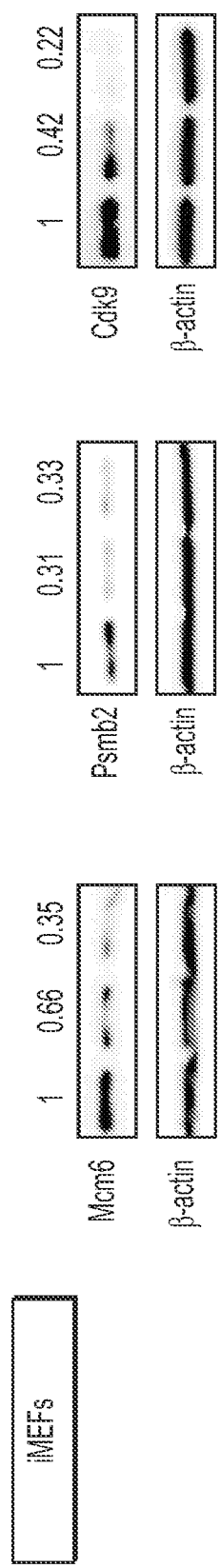
(FIG. 2D) Immunoblots showing the knockdown induced by shRNAs expressed from TRMPV-neo in iMEFs. β-actin was used as loading control.

To identify targets whose inhibition showed selective anti-proliferative effects in cancer cells, the positive hits above in the MP1 cells used in the screen were validated, and then those that showed a similar effect on non-transformed immortalized mouse embryo fibroblasts (iMEFs) were filtered out. shRNAs targeting Rpa3, an essential gene, and Myc, the oncogenic driver in the screened MP1 cell line, were used as positive-controls; a Renilla luciferase shRNA was used as negative-control. All selected shRNAs produced a competitive disadvantage in MP1 cells (FIG. 2A), confirming that the screen performance and the selection criteria were sufficient to remove false positive events. Moreover, each validated shRNA showed substantial knockdown of the intended protein, further indicating that the observed phenotypes were due to on-target effects (FIG. 2B).

shRNAs targeting Mcm6 and Psmb2 inhibited iMEFs and MP1 cells to a similar extent, suggesting that inhibition of their target proteins was generally lethal, much like the control Rpa3 shRNA (FIGS. 2C and 2D). By contrast, CDK9 shRNAs showed a reduced ability to inhibit proliferation in iMEFs as compared to MP1 cells (FIGS. 2C and 2D), an effect that was similar to the Myc shRNA and could not be accounted for by differences in proliferation rates of iMEFs and MP1 cells or in shRNA knockdown (FIGS. 2B and 2D). Owing to this apparent specificity, CDK9 became a candidate for more detailed analysis.

Figure 2E:
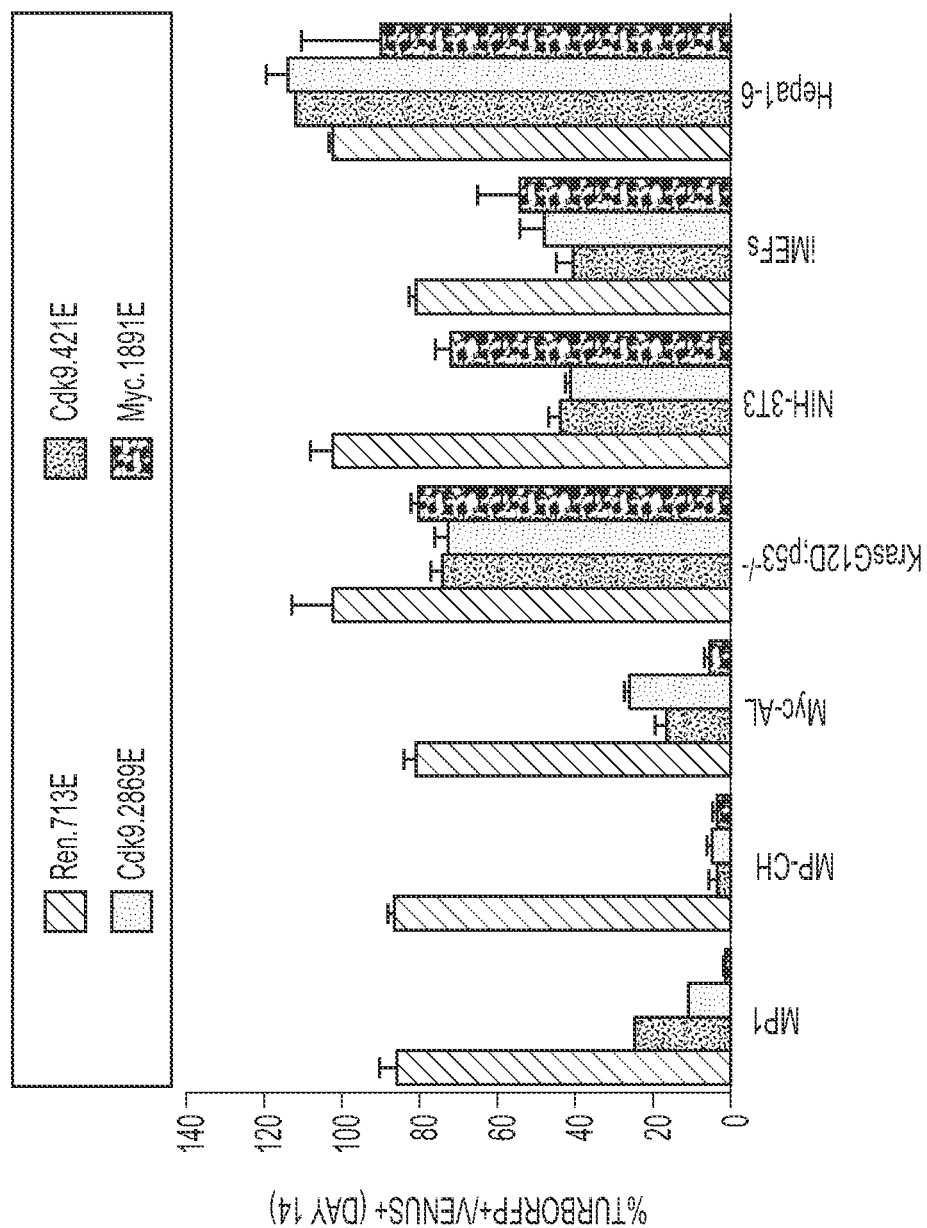
(FIGS. 2E and 2F) Competitive proliferation assay of control (Renilla and MYC) and CDK9 shRNAs expressed from TRMPV-neo-miR-E (FIG. 2E) or TRMPV-neo (FIG. 2F) in different murine (FIG. 2E) and human cell lines (FIG. 2F), as described in FIG. 2A. The percentage of shRNA-expressing cells at day 14 relative to day 0 is shown. MP1, Myc;p53−/− murine HCC clone #1 cells; The "E" letter after the name of the shRNA indicates that the shRNA is cloned into miR-E backbone instead of miR-30.
Figure 2F:
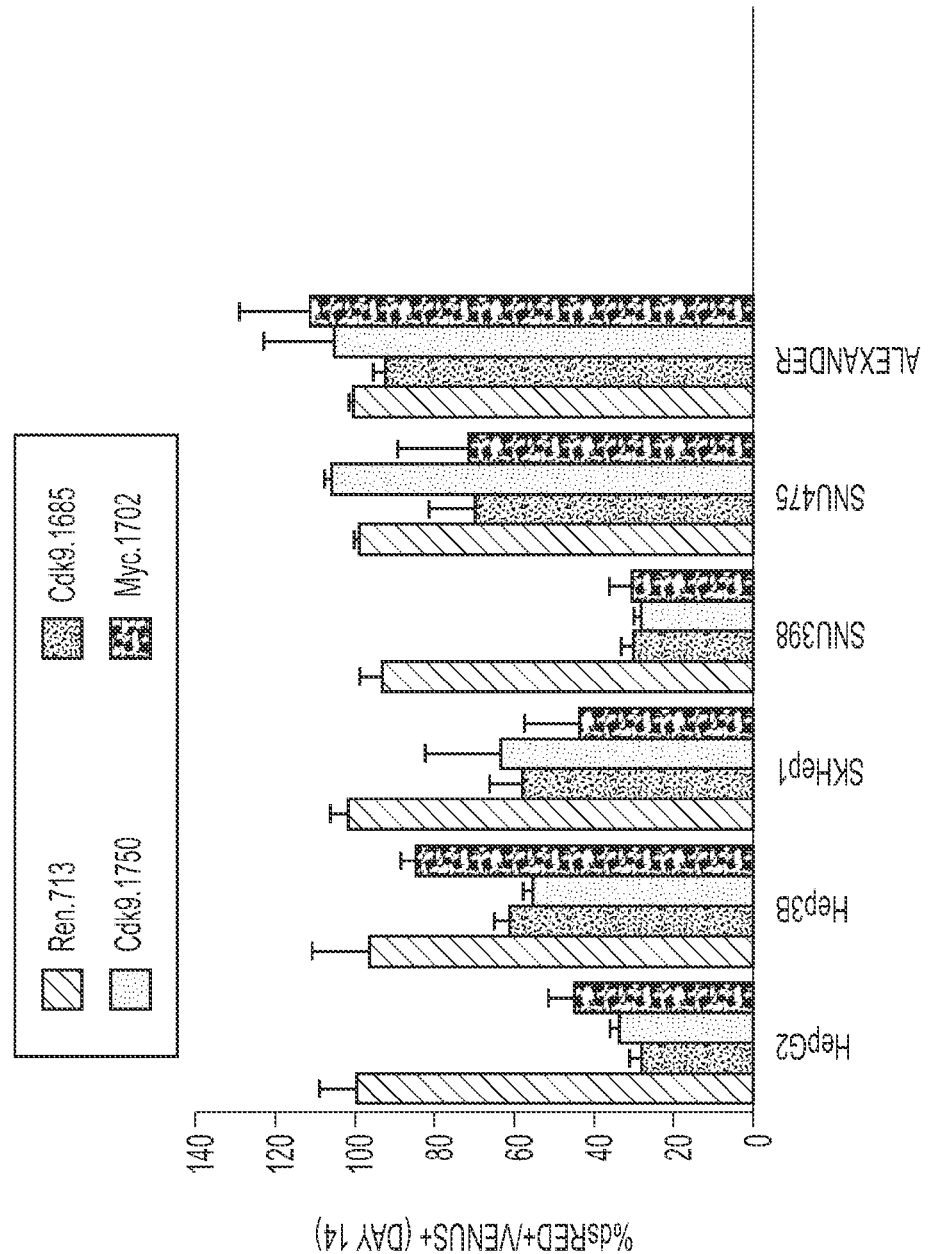

To confirm that the impact of CDK9 inhibition on cancer cell proliferation was not limited to one experimental HCC line, additional murine and human cell lines engineered to express rtTA3 to allow dox-dependent shRNA induction were studied. Control (Renilla and Myc) and CDK9 shRNAs were subcloned into miR-E, an optimized miR-30-based backbone that increases knockdown efficiency, particularly for those shRNAs with intermediate potency. All three experimental murine HCC cell lines that overexpressed Myc were sensitive to CDK9 inhibition, while murine HCC cells expressing mutant KrasG12D, Hepa1-6 hepatoma cells, NIH-3T3 fibroblasts, and iMEFs showed modest to no sensitivity (FIG. 2E). Similarly, human HCC cell lines showed a range of responses to human CDK9 shRNAs with some being highly sensitive and others more resistant (FIG. 2F). Again, these differential responses were independent of the proliferation rates of various cell lines and the extent of CDK9 knockdown. Together, these results indicate that that pharmacological inhibition of CDK9 may have a therapeutic effect against certain cancers, such as HCC, leukemia, lymphoma and NSCLC.

Figure 3A:
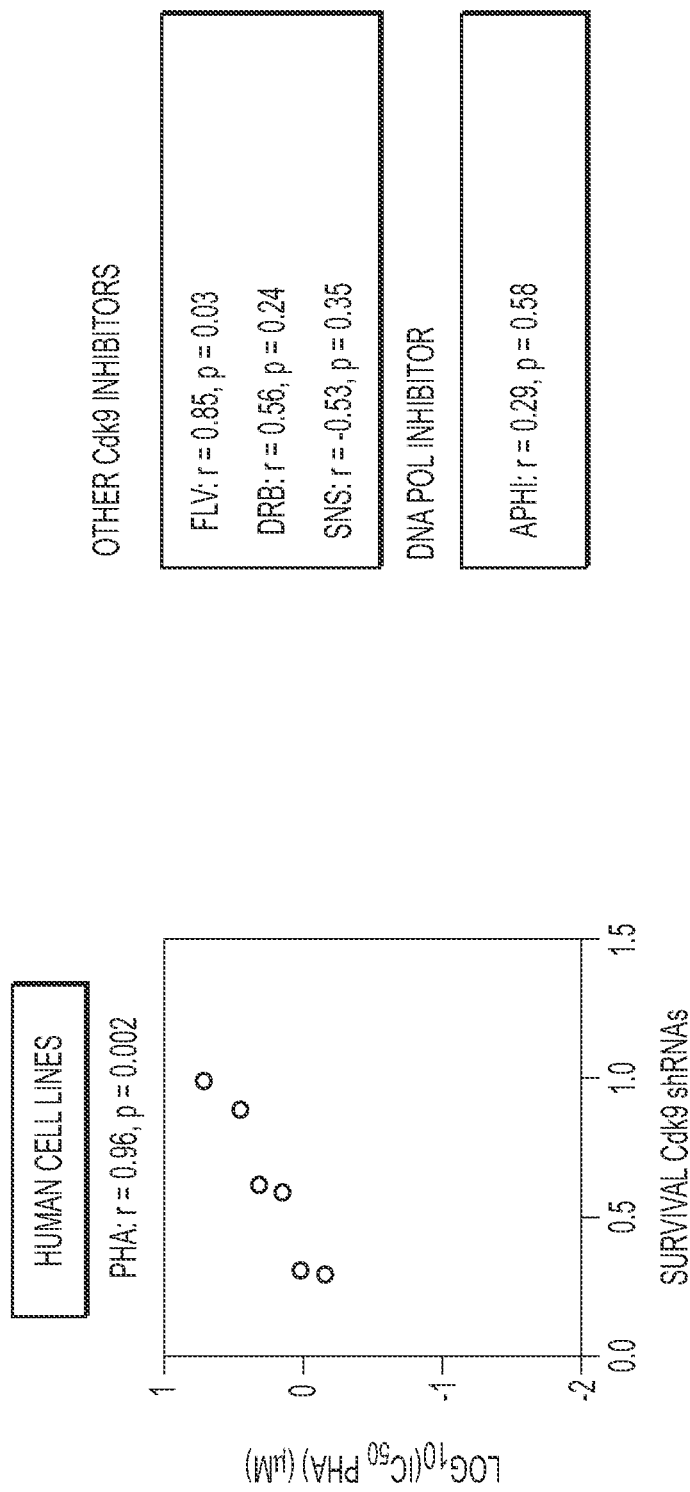
(FIG. 3A) Scatter plot illustrating the correlation between anti-proliferative effects of CDK9 shRNAs and the IC50 of PHA-767491 in six human cell lines. The correlation and p values of three additional CDK9 inhibitors and one DNA replication inhibitor (aphidicolin) are also shown in the right panel. The survival is defined as the average of the survival ratio of two shRNAs in competitive proliferation assay.
Figure 3B:
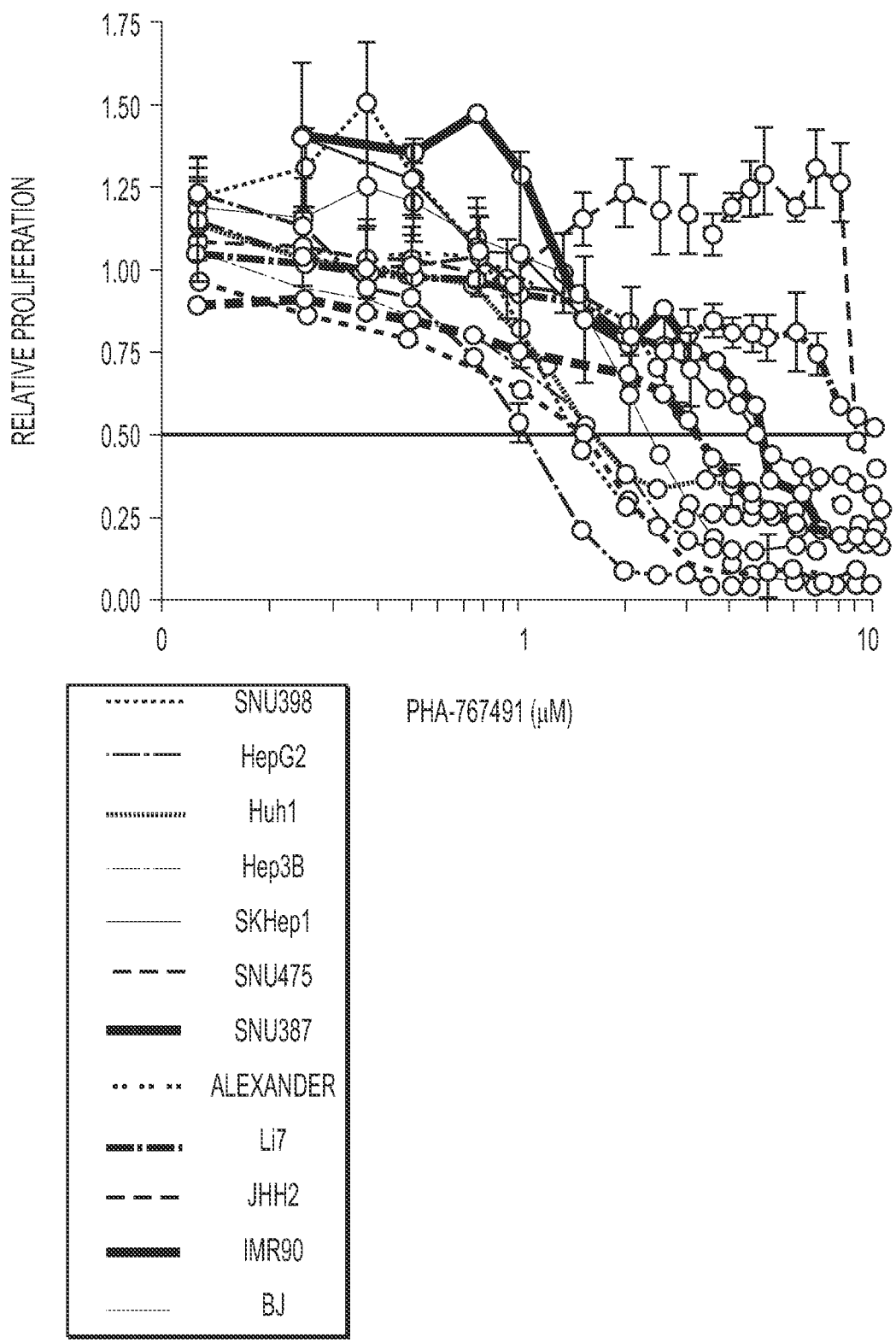
(FIG. 3B) Proliferation rates of PHA-767491-treated human cells, calculated by measuring the change in viable cell number after 72 h in culture and fitting data to an exponential growth curve. Results were normalized to the proliferation rate of vehicle (H2O) treated cells, set to 1. Values are mean+/−SD of three independent replicates.
Figure 3D:
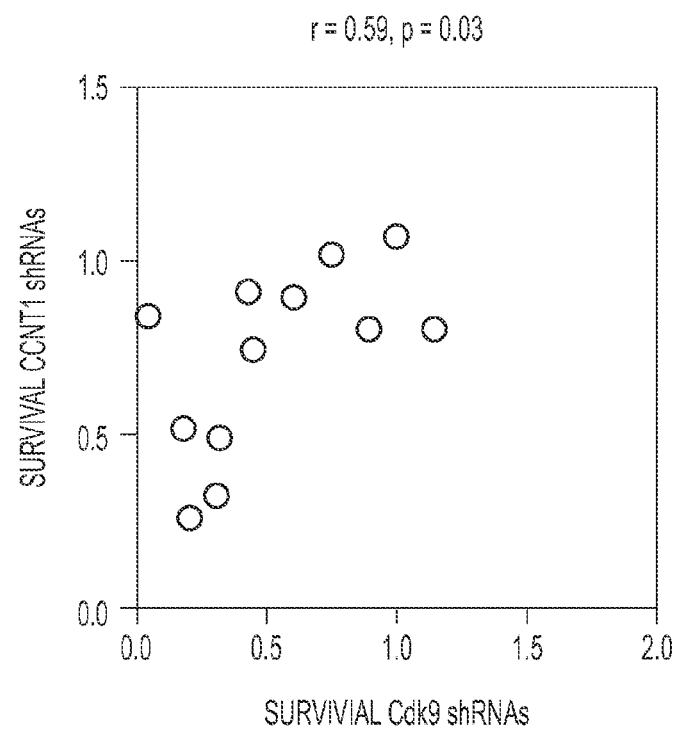
(FIG. 3D) Scatter plot illustrating the correlation between survival with CCNT1 shRNAs and survival with CDK9 (black), in murine and human cell lines.

Available CDK9 inhibitors whose biology is most closely related to CDK9 inhibition may show a spectrum of activity similar to CDK9 shRNAs. The IC50 of several CDK9 inhibitors was compared with the anti-proliferative effects of CDK9 shRNAs in competitive proliferation assays (FIGS. 2E and 2F). After testing four different CDK9 inhibitors, results identified PHA-767491, a dual CDK9 and CDC7 (cell division cycle 7) kinase inhibitor, most closely recapitulated shRNA-mediated CDK9 inhibition in both human and murine cell lines (FIGS. 3A-3C). Notably, CDC7 in complexes with its allosteric regulator, DBF4, is required for initiation of DNA replication. However, exposure of cells to aphidicolin, an inhibitor of DNA polymerase, did not mimic the effects of CDK9 shRNAs (FIG. 3A). In contrast, shRNAs directed to Cyclin T1 (CCNT1), an obligate allosteric regulator of the CDK9 kinase, recapitulated the results obtained with CDK9 shRNAs (FIG. 3D), thereby highlighting the specificity of these results.

Figure 3E:
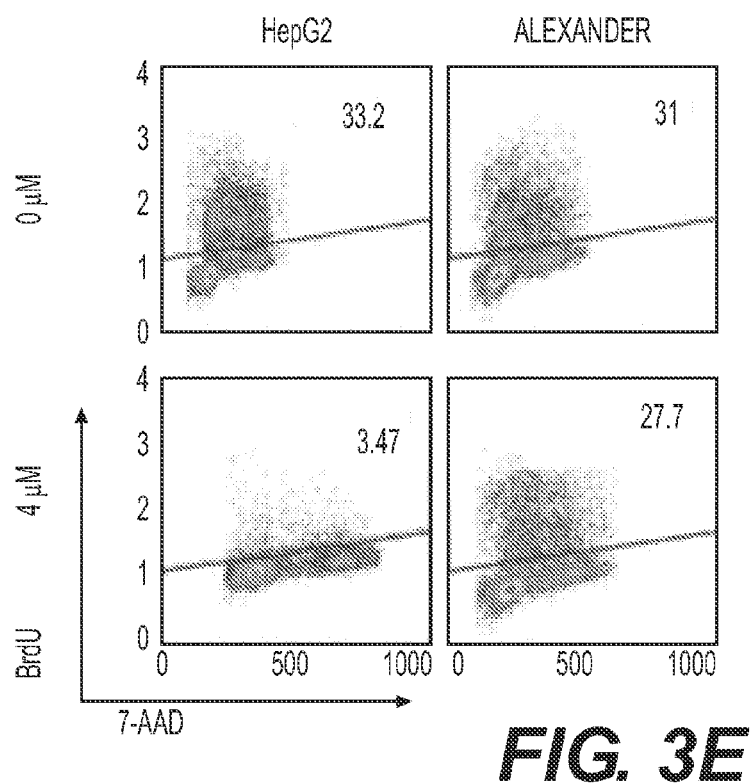
(FIG. 3E) Representative flow cytometry plots showing cell cycle analysis (BrdU+7-AAD+ double staining) of cells after 48 hours of PHA-767491 treatment. The experiment was performed twice and values indicate the mean+SD. r, Pearson correlation coefficient; FLV, flavopiridol; PHA, PHA-767491; SNS, SNS-032; APHI, aphidicolin.

The effect of PHA-767491 in additional human HCC cell lines (FIGS. 3B and 3C) was evaluated. and broad anti-proliferative activity in the most sensitive cell lines was observed (IC50<2 M) (FIG. 3E). PHA-767491 treatment triggered cell-cycle arrest, similar to the effects of CDK9 shRNAs (FIG. 3E); however, the anti-proliferative effects mediated by PHA-767491 were more pronounced. Of note, two non-transformed cell lines were consistently less sensitive to PHA-767491 treatment (FIGS. 3B and 3C), further supporting increased sensitivity of certain cancer cells to CDK9 inhibition. While some of these phenotypes may be due to CDC7 inhibition, the significant correlation between the IC50 of PHA-767491 and the anti-proliferative effects of CDK9 shRNAs implies that a major component of PHA-767491 activity is through CDK9 inhibition. These data illustrate how using RNAi and small molecule inhibitors as orthogonal approaches can assist target validation and indicate that CDK9 can be required for HCC proliferation.

Example 4

Predicting Response to CDK9 Inhibition

Figure 4A:
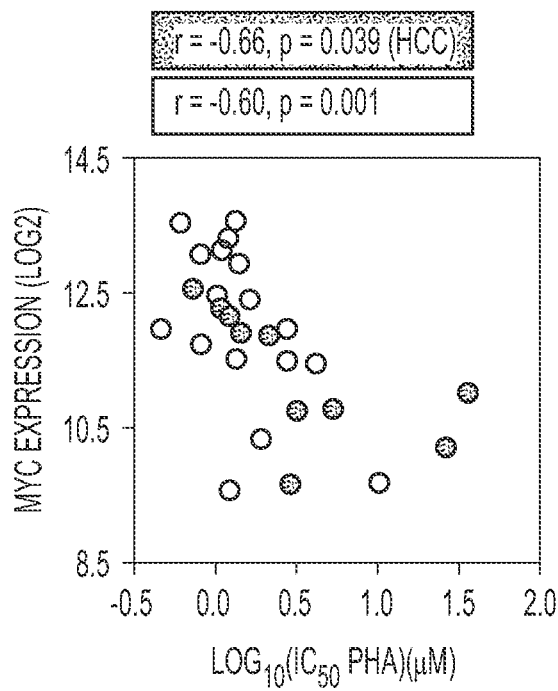
(FIG. 4A) Scatter plot illustrating the correlation between PHA-767491 IC50 values and MYC expression levels in human HCC (red), leukemia, lymphoma, and lung cancer cell lines (n=28).
Figure 4B:
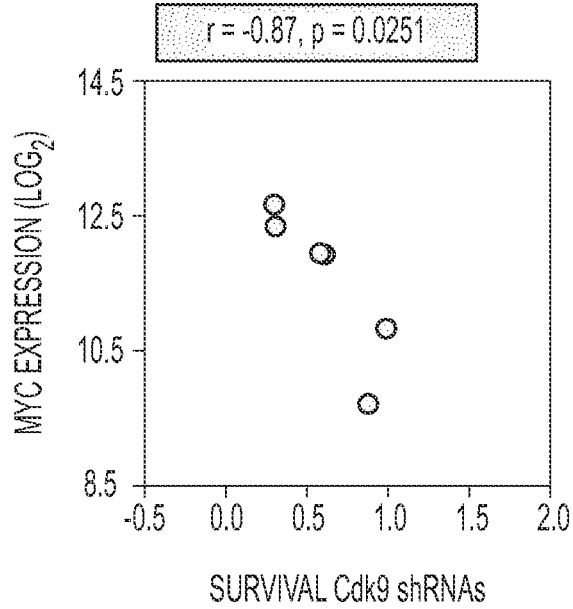
(FIG. 4B) Scatter plot illustrating the correlation between survival with CDK9 shRNAs and MYC expression levels in a panel of different human HCC cell lines. The survival is defined as the average of the survival ratio of two shRNAs in competitive proliferation assay.
Figure 4C:
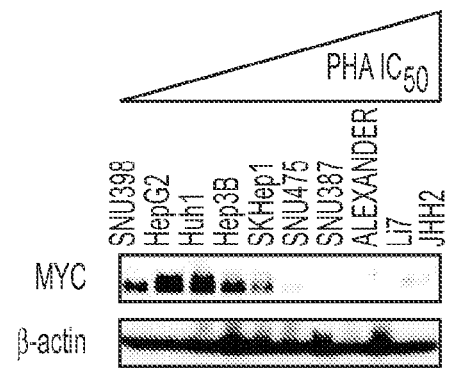
(FIG. 4C) Immunoblots showing MYC protein levels in 10 human HCC cell lines. β-actin was used as loading control.

Since the screening system was driven by p53 loss and Myc overexpression, alterations in either gene could dictate sensitivity to CDK9 inhibition. Data on the relative sensitivity of HCC cell lines to CDK9 inhibition (measured as the growth-inhibitory effects of CDK9 shRNAs in competitive proliferation assays or the IC50 of PHA-767491) was cross-referenced to mutational and gene expression profiles of the same cell lines available from the Cancer Cell Line Encyclopedia (CCLE). The cross-referencing found no correlation between the anti-proliferative response to CDK9 inhibition and p53 expression or mutational status, consistent with previous findings indicating that PHA-767491 inhibits cancer cell proliferation through p53-independent mechanisms. However, there was a highly significant correlation between the response to CDK9 inhibition and MYC mRNA expression (FIGS. 4A and 4B), an effect that was confirmed by immunoblotting for MYC protein (FIG. 4C). This significant correlation was not limited to HCC cell lines but was also observed in a panel of lung and hematopoietic cancer cell lines (FIG. 4A). In all instances, no correlation was observed between sensitivity to CDK9 inhibition and the relative proliferative rates of individual cell lines nor was sensitivity related to MYC amplification, indicating that MYC expression, rather than MYC amplification status, is associated with the response to CDK9 inhibitors.

Figure 4D:
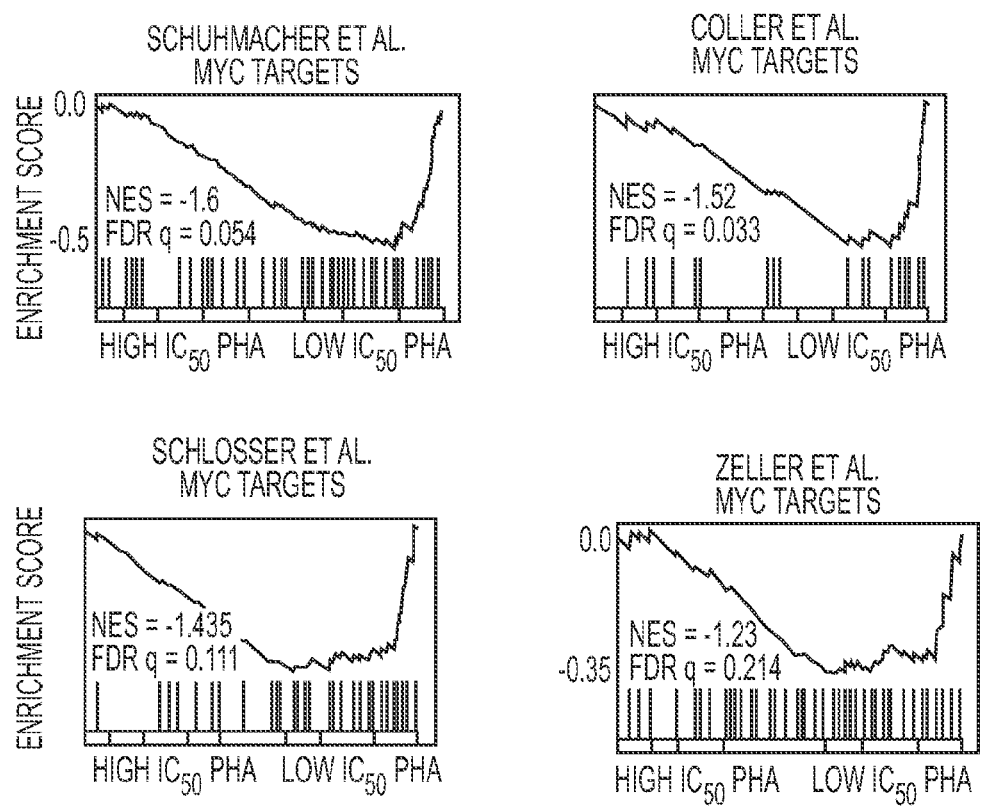
(FIGS. 4D and 4E) GSEA plot evaluating the association between low $IC_{50}$ of PHA-767491 and MYC targets (FIG. 4D) or a MYC-overexpressing subclass of HCC patients (FIG. 4E). GO-term analysis of the genes that are significantly associated with sensitivity to PHA-767401. r, Pearson correlation coefficient; PHA, PHA-767491; NES, normalized enrichment score; FDR, false discovery rate can be provided.
Figure 4E:
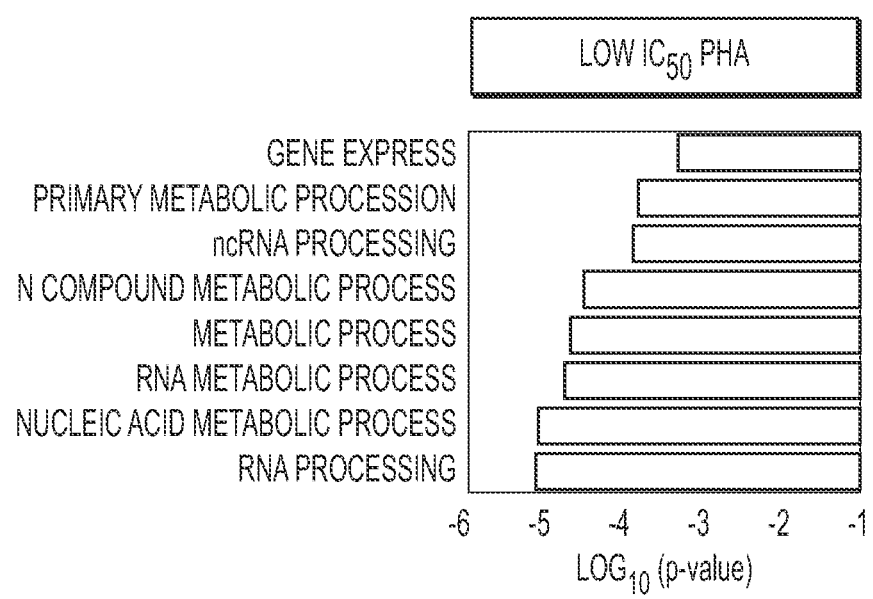

The transcriptional profiles of the 10 human HCC cell lines with defined sensitivities to PHA-767491 were also subjected to Gene Set Enrichment Analysis (GSEA) and Gene ontology (GO) analysis to point towards genes and processes that might underlie their differential sensitivity. This analysis revealed a significant correlation between low IC50 (sensitivity to CDK9 inhibition) and four canonical transcriptional signatures of MYC-dependent genes (FIG. 4D), and a gene signature that defines a subclass of HCC patients characterized by MYC and AKT activation (FIG. 4E). By contrast, there was an inverse correlation between a gene expression signature related to a different subclass of HCC patients with WNT pathway activation and sensitivity to the drug. MYC is a global regulator of gene expression that affects overall transcription, ribosomal biogenesis, protein translation, and cellular metabolism, and interestingly transcripts overrepresented in sensitive compared to resistant cells were linked to "gene expression", "RNA metabolic process" and "RNA processing" (FIG. 4F). Taken together, these results indicate that CDK9 might be crucial for the maintenance of MYC-overexpressing tumors, and identify a potential patient population that might be sensitive to CDK9 inhibition.

After transcription initiation, RNA pol II is trapped near the promoter of many genes, a process known as proximal promoter pausing. For productive transcription, P-TEFb is recruited, and CDK9 phosphorylates Ser2 in the C-terminal domain (CTD) of RNA pol II, inducing pause-release and subsequent transcription elongation. MYC has previously been shown to participate in transcription elongation by regulating this pause release mechanism. Thus, in MYC-overexpressing tumor cells, MYC accumulates in the promoter region of many transcriptionally active genes, recruiting the P-TEFb complex and amplifying transcription of MYC-target genes.

Figure 5A:
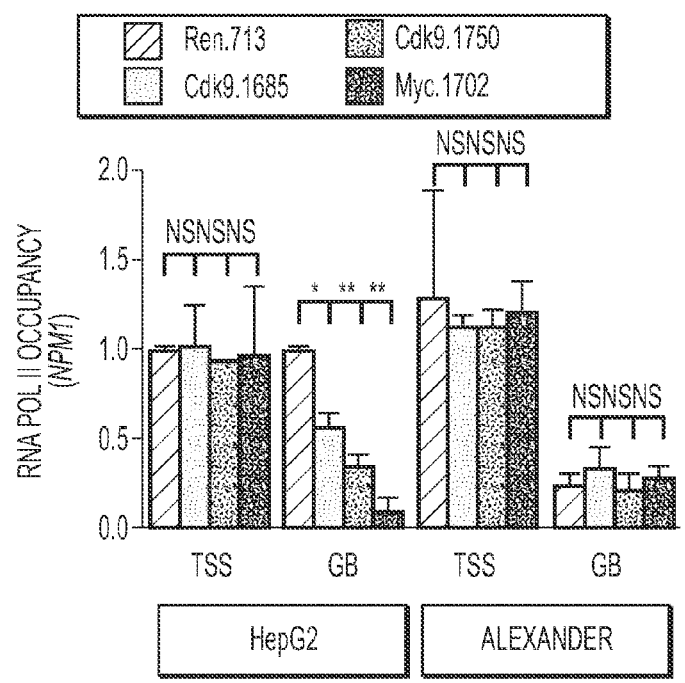
(FIGS. 5A and 5B) ChIP-qPCR performed in human HCC cells expressing CDK9 and MYC shRNAs (FIG. 5A) or treated with PHA-767491 (6 hours at 4.5 µM) (FIG. 5B) with RNA pol II antibody and primers located either in the transcription start site (TSS) or in the gene body (GB) of NPM1.
Figure 5B:
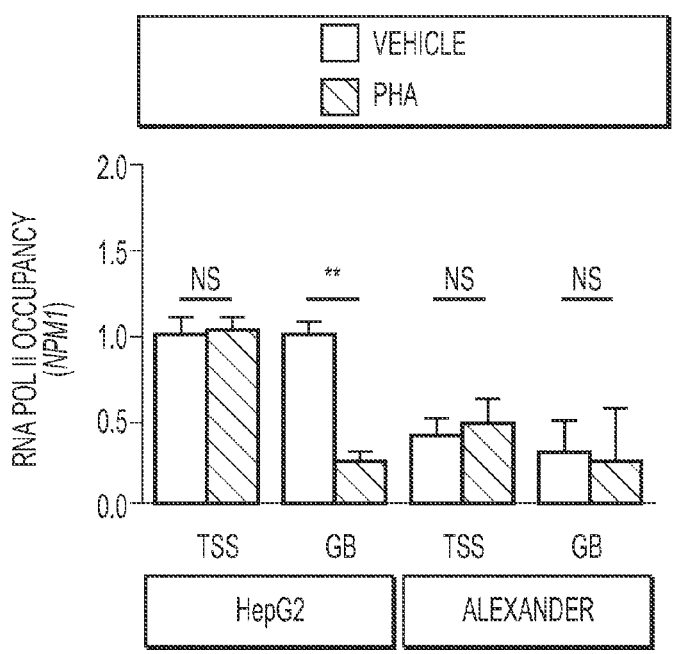
Figure 5C:
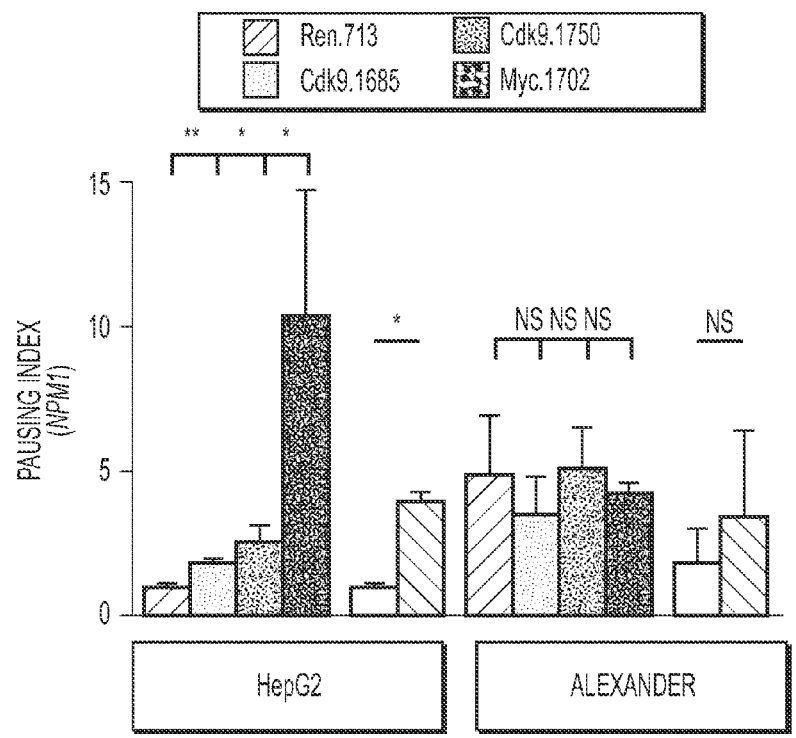
(FIG. 5C) Pausing index of NPM1 in human HCC cell lines. The pausing index, also known as traveling ratio, is calculated as the ratio between the RNA pol II bound to the TSS and the RNA pol II bound to the GB. Color code and statistics as in FIGS. 5A and 5B.
Figure 5D:
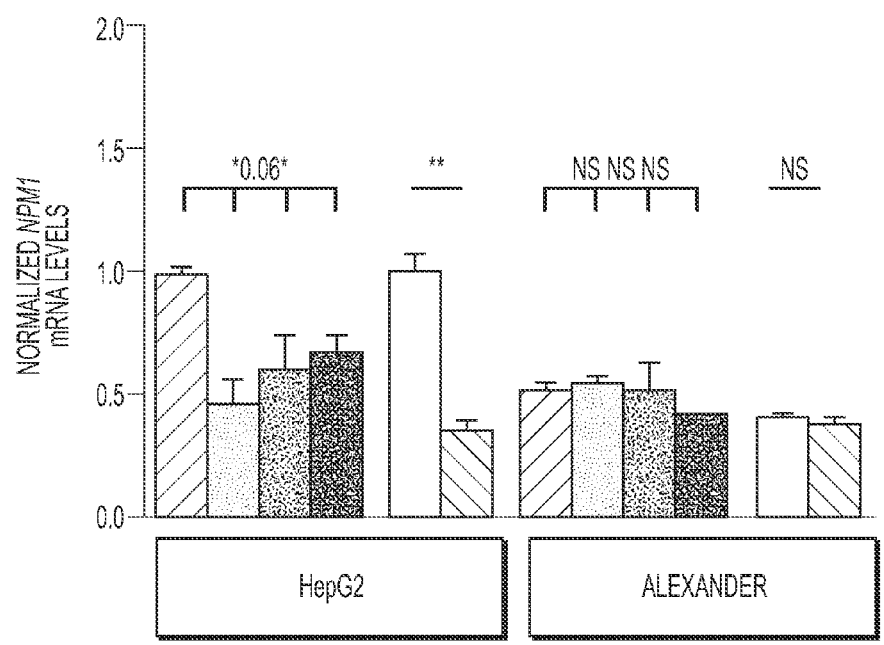
(FIG. 5D) Quantitative RT-PCR of NPM1 in human HCC cell lines treated with PHA-767491 (16 hours at 4.5 M) or with CDK9 shRNAs. Data are relative to expression in the untreated cells or Renilla-shRNA in HepG2 cells, normalized to the average expression of the housekeeping gene GAPDH. Values are mean±SD from two independent experiments. Color code and statistics as in FIGS. 5A and 5B. PHA, PHA-767491.
Figure 5E:
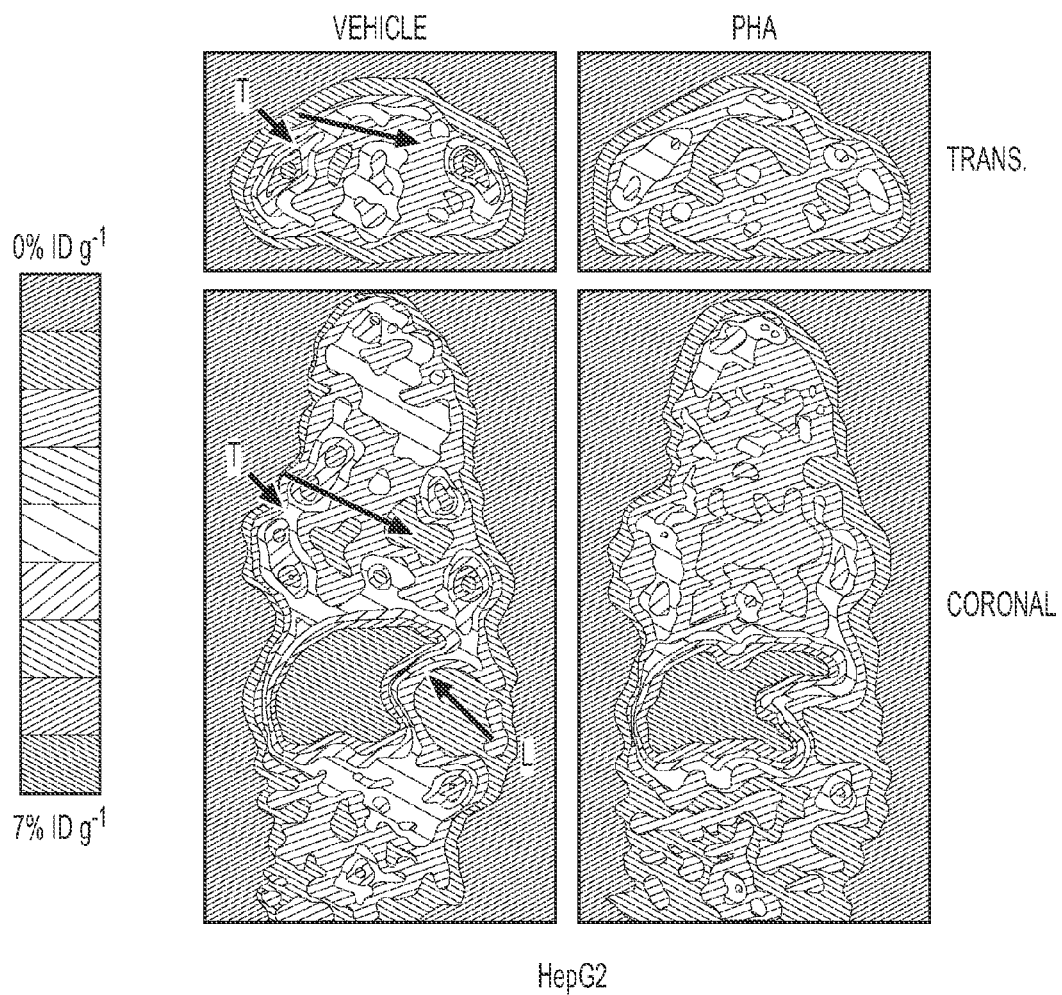
(FIGS. 5E and 5F) PET imaging with $^{89}$Zr-transferrin of HepG2 (E) or Alexander (F) tumors with or without 3-d treatment with PHA-767491. (L) Liver; (T) tumor; (trans.) transverse. The hashmark scale for all PET image data shows radiotracer uptake in units of injected dose per gram (% ID/g), with diagonal hashmarks sloping left corresponding to the highest activity, and diagonal hashmarks sloping right corresponding to the lowest activity.
Figure 5F:
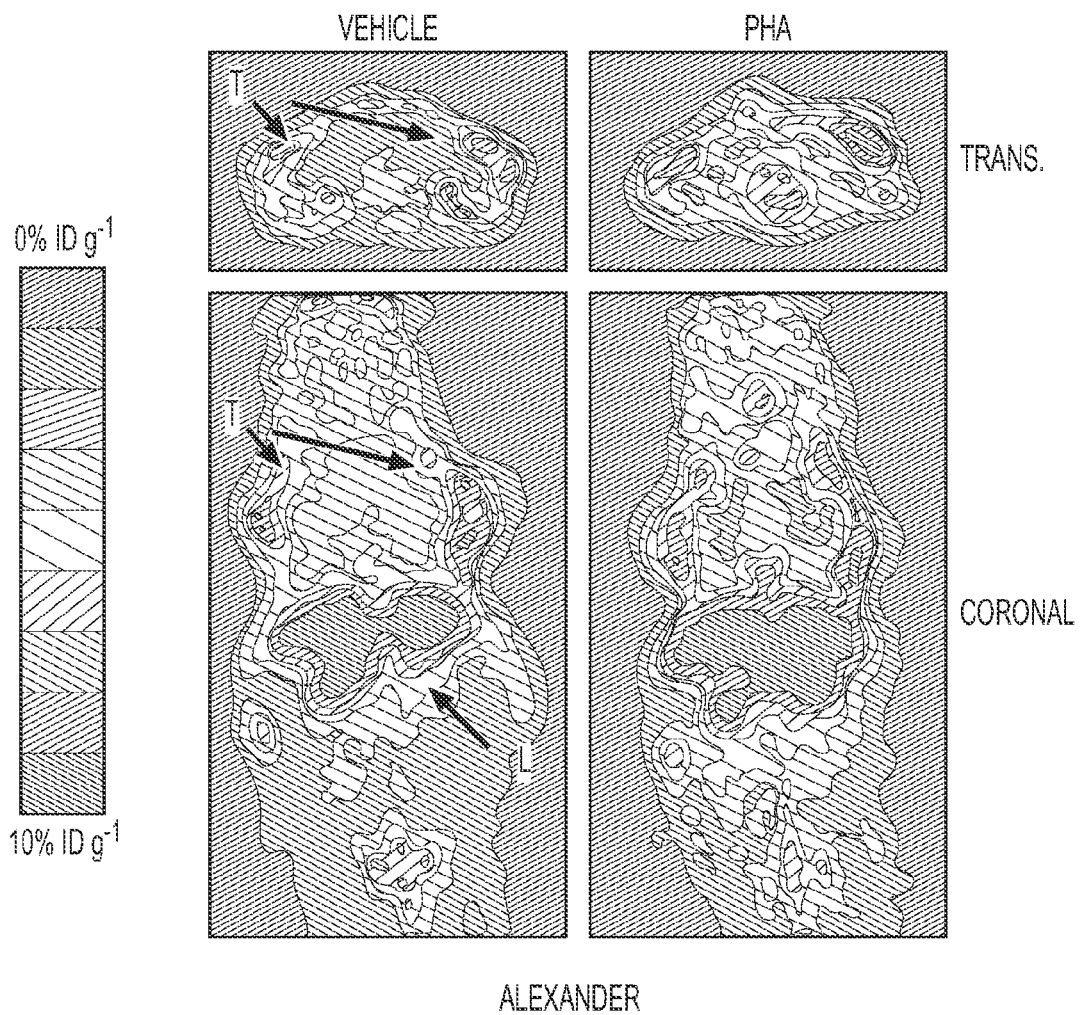

To explore the role of CDK9 in MYC-mediated transcriptional amplification, the effects of CDK9 inhibition in two human HCC cell lines, HepG2 and Alexander, which express different levels of MYC, were investigated (FIG. 4C). As expected, pharmacological or RNAi-mediated suppression of CDK9 led to a decrease in Ser2 phosphorylation in both cell lines. In order to investigate whether these changes correlated with changes in transcription elongation, the investigation calculated the pausing index or travelling ratio in which the ratio of RNA Pol II binding density in the proximal promoter region is compared with that in the gene body. In HepG2 cells expressing high levels of MYC, inhibition of CDK9 (using small molecules or shRNAs) or MYC caused a significant repression of transcription elongation of NPM1 and MCM4, two select MYC targets, and an increase in their pausing index (FIGS. 5A-5C). However, no changes were observed for BRG1, whose transcription is not impacted by MYC. In contrast, Alexander cells expressing much lower MYC levels, the pausing index at the NPM1 and MCM4 genes was already high in untreated cells and did not change substantially following CDK9 or MYC inhibition (FIG. 5C). Accordingly, CDK9 or MYC inhibition reduced mRNA levels of MYC target genes in HepG2 cells but not Alexander cells (FIG. 5D). Together, these results indicate that CDK9 regulates the transcription elongation of MYC targets NPM1 and MCM4 in the context of high MYC expression, and that CDK9 inhibitors can reverse these effects.

Example 5

Competitive Proliferation Assays

Figure 6A:
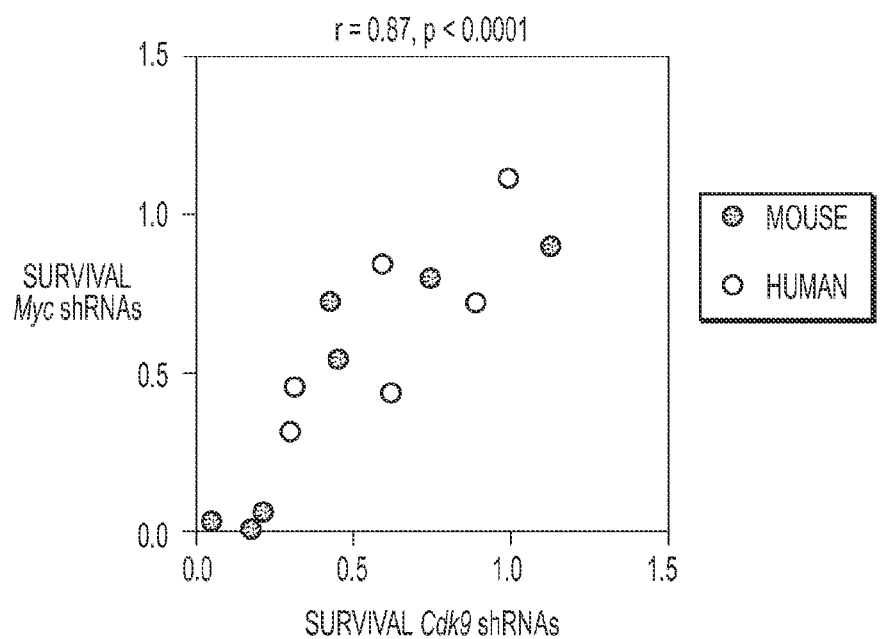
(FIGS. 6A and 6B) Scatter plot illustrating the correlation between survival with MYC shRNAs and with CDK9 shRNAs in mouse and human cell lines (FIG. 6A) and with CCNT1 shRNAs (B). The survival is defined as the ratio of surviving cells in the competitive proliferation assays (FIGS. 2E and 2F). In the case of CDK9 and CCNT1, the average of the survival of two different shRNAs is used.
Figure 6B:
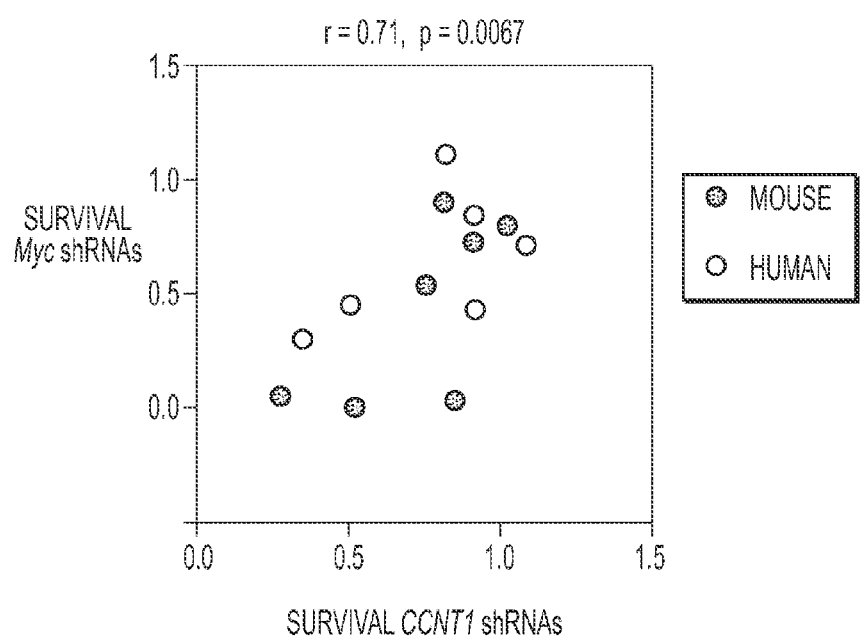

MYC has been implicated in DNA replication, transcriptional activation, transcription elongation and other processes, though the relative contribution of each process to tumor initiation and maintenance is not well understood. Despite the diversity of factors involved in these processes, CDK9 and MYC shRNAs displayed similar depletion patterns across multiple lines (FIGS. 2E and 2F) and, in fact, there was a significant correlation between the anti-proliferative effects of CDK9 and MYC shRNAs in competitive proliferation assays (FIG. 6A). A similar correlation existed between the anti-proliferative effects of Cyclin T1 and Myc shRNAs (FIG. 6B).

Figure 6C:
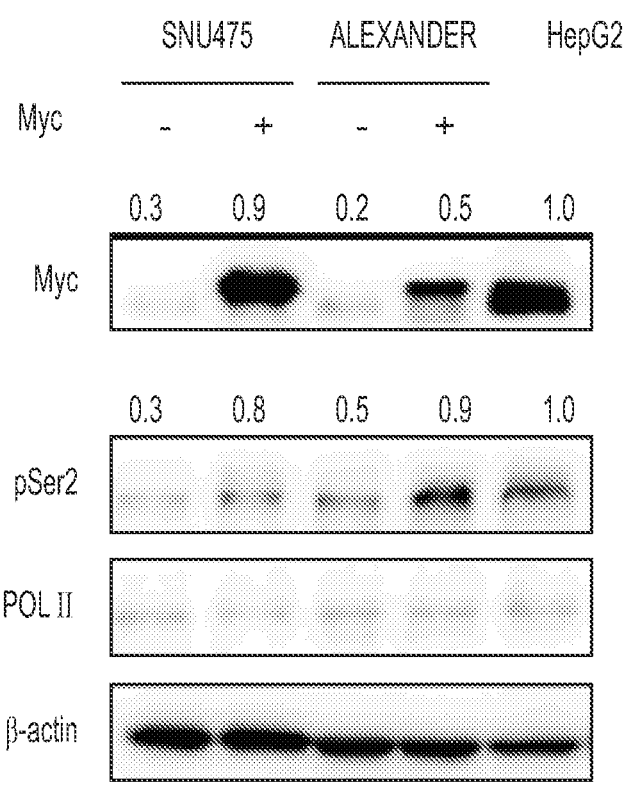
(FIG. 6C) Immunoblots showing MYC overexpression effect on Ser2 phosphorylation of RNA Pol II in low MYC-expressing SNU475 and Alexander cells. β-actin was used as loading control. Values indicate normalized protein levels, normalized with β-actin or RNA Pol II, and relative to the levels in HepG2 cells.
Figure 6D:
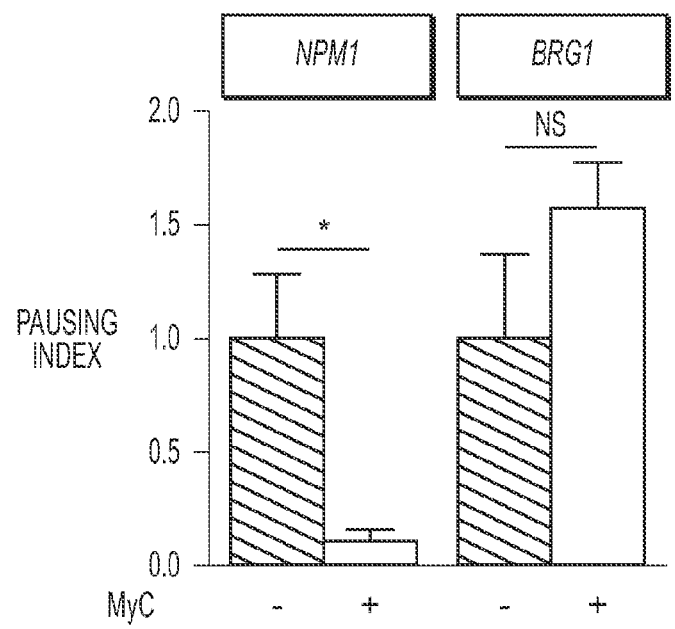
(FIG. 6D) Pausing index of NPM1 and BRG1 in Alexander cells overexpressing MYC. Pausing index, also known as traveling ratio, is calculated as the ratio between the RNA pol II bound to the transcription start site and the RNA pol II bound to the gene body.
Figure 6E:
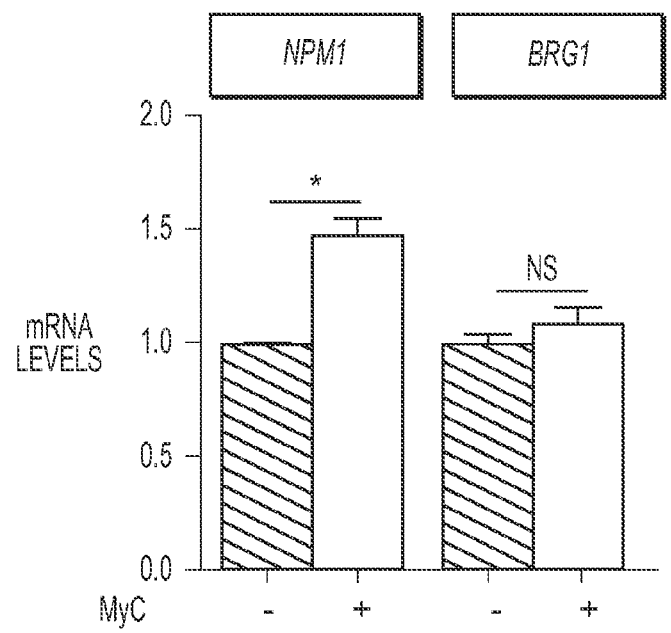
(FIG. 6E) Quantitative RT-PCR of NPM1 and BRG1 in Alexander cells overexpressing MYC. Data are relative to expression in the cells expressing an empty vector, normalized to the average expression of the housekeeping gene GAPDH. Values are mean+SD from two independent experiments.
Figure 6F:
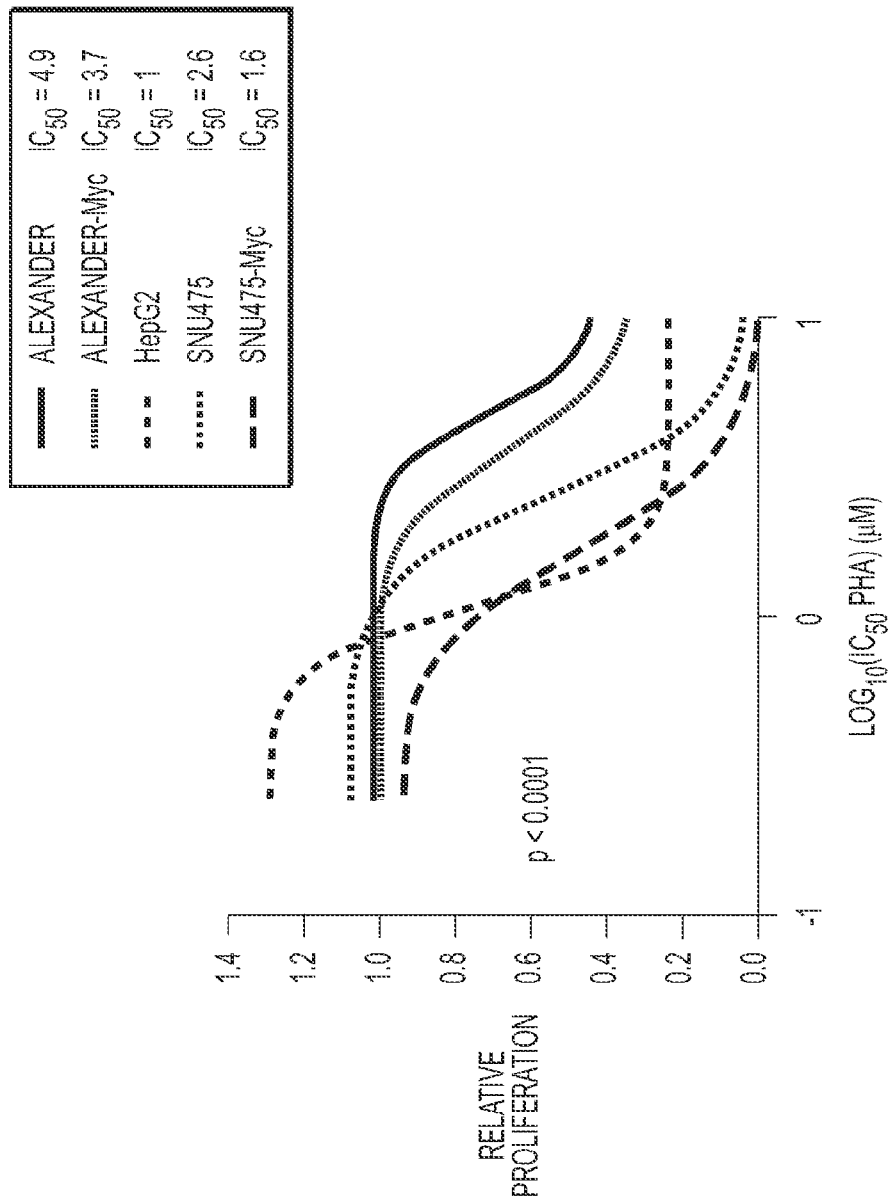
(FIG. 6F) Proliferation rates of PHA-767491-treated cells in FIG. 6C, calculated by measuring the increase in viable cell number after 72 h in culture and fitting data to an exponential growth curve. Results are normalized to the proliferation rate of vehicle (H2O) treated cells, set to 1. Values are mean+SD of two independent replicates. The IC50 values are included in M.
Figure 6G:
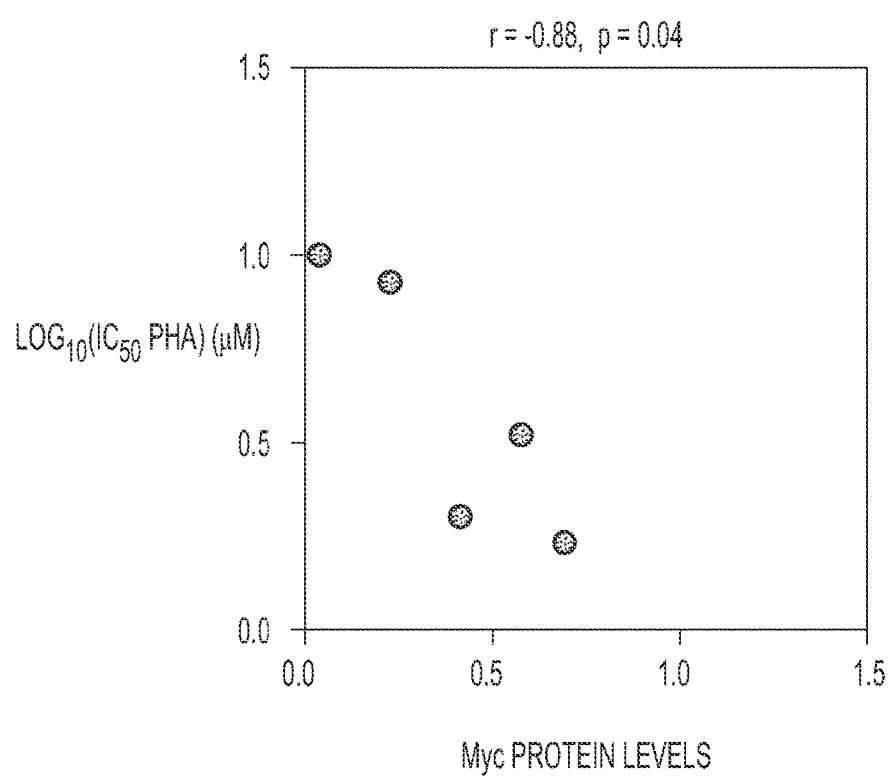
(FIG. 6G) Scatter plot illustrating the correlation between MYC protein levels and the IC50 of PHA-767491 on the different cell lines in FIG. 6F. The "E" letter after the name of the shRNA indicates that the shRNA is cloned into miR-E backbone instead of miR-30; PHA, PHA-767491; r, Pearson correlation coefficient.

To directly determine whether modulation of MYC activity could influence cellular dependence on CDK9 activity, the experiment tested the ability of enforced MYC expression to influence sensitivity to CDK9 inhibition. Ectopic MYC expression in the low MYC Alexander cells produced MYC levels ~50% of those measured in sensitive HepG2 cells and an increase in MYC-dependent transcription elongation as measured by a reduced pausing index at the NPM1 and MCM4 but not BRG1 genes (FIGS. 6C and 6D). This effect on transcription elongation was accompanied by significant increases in NPM1 and MCM4 mRNAs (FIG. 6E), while levels of BRG1 mRNA did not change (FIG. 6E). Concordantly, MYC-overexpressing Alexander cells became more sensitive to CDK9 inhibition by PHA-767491 or CDK9 shRNAs (FIG. 6F). While enforced MYC expression in these cells did not produce the same sensitivity of high MYC-expressing HepG2 cells, enforced MYC expression in SNU-475 cells achieved MYC levels equivalent to those observed in HepG2 cells (FIG. 6C) and produced a similar sensitivity to PHA-767491 (FIGS. 6F and 6G). The phenotypic similarities between MYC inhibition and CDK9/CCNT inhibition indicate a key role for transcription elongation in mediating MYC action in tumor maintenance.

Example 6

Figure 7A:
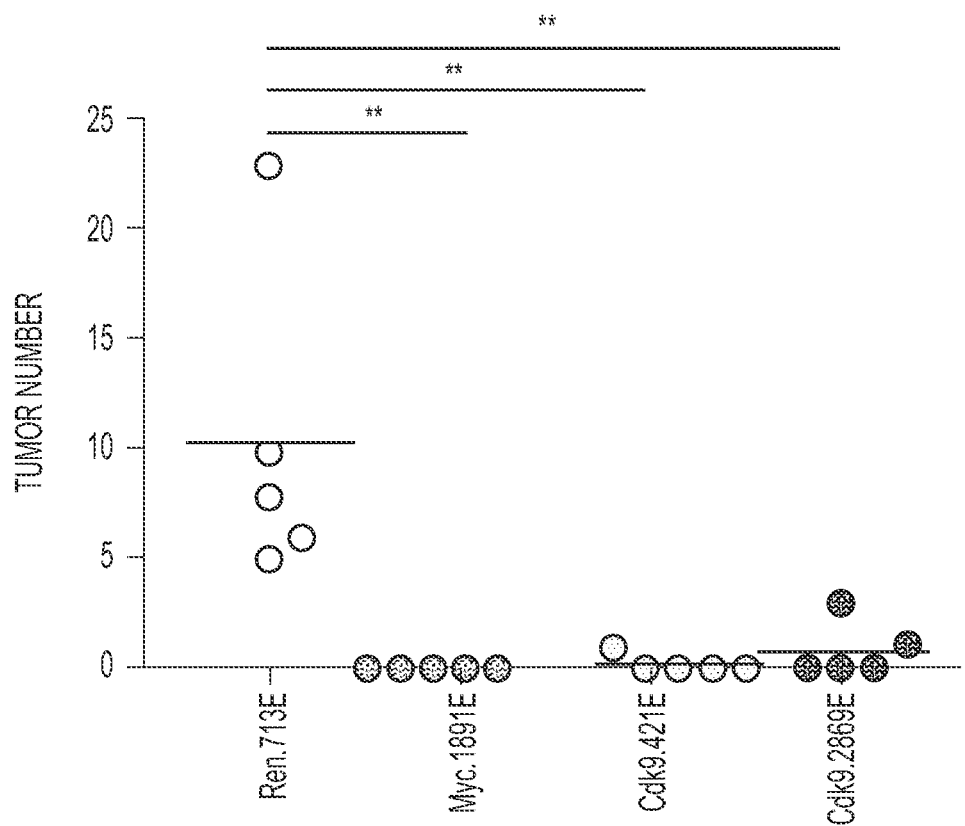
(FIG. 7A) Dot plot representation of the number of liver tumors after the hydrodynamic injection of Myc oncogene and the corresponding shRNAs. Bars represent the mean±SD of five independent mice.
Figure 7B:
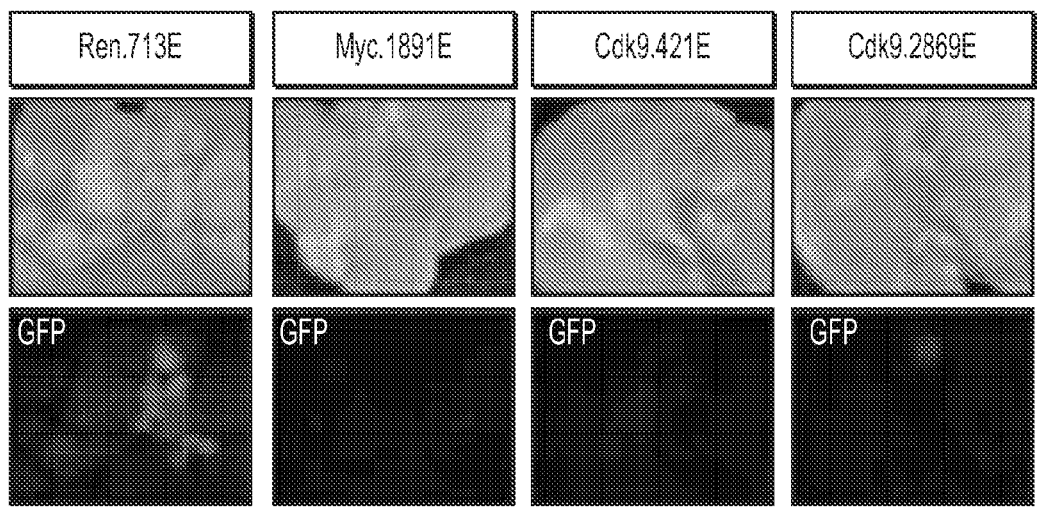
(FIG. 7B) Representative bright-field and fluorescent images of the livers in A. Tumors are positive for GFP.
Figure 7C:
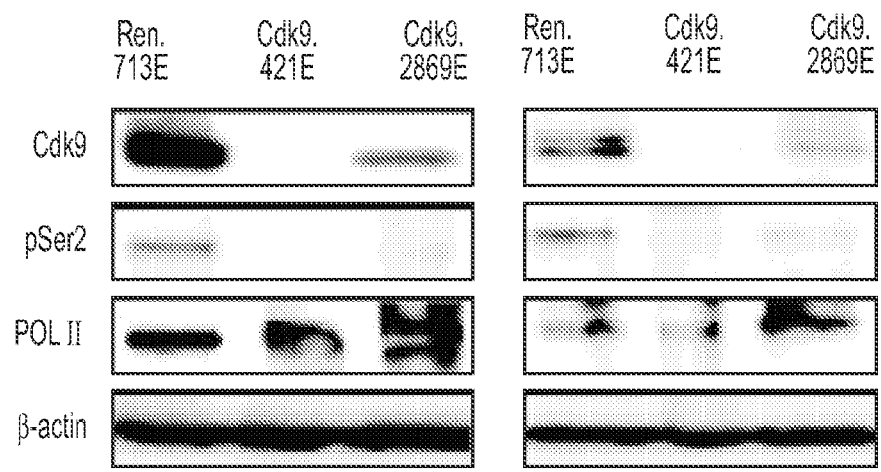
(FIG. 7C) Immunoblots showing the knockdown induced by CDK9 shRNAs in two representative tumors. CDK9 inhibition leads to a decrease in the levels of phosphorylation of Ser2 of RNA pol II (pSer2) and mild changes in total RNA pol II levels (Pol II). β-actin was used as loading control.
Figure 7D:
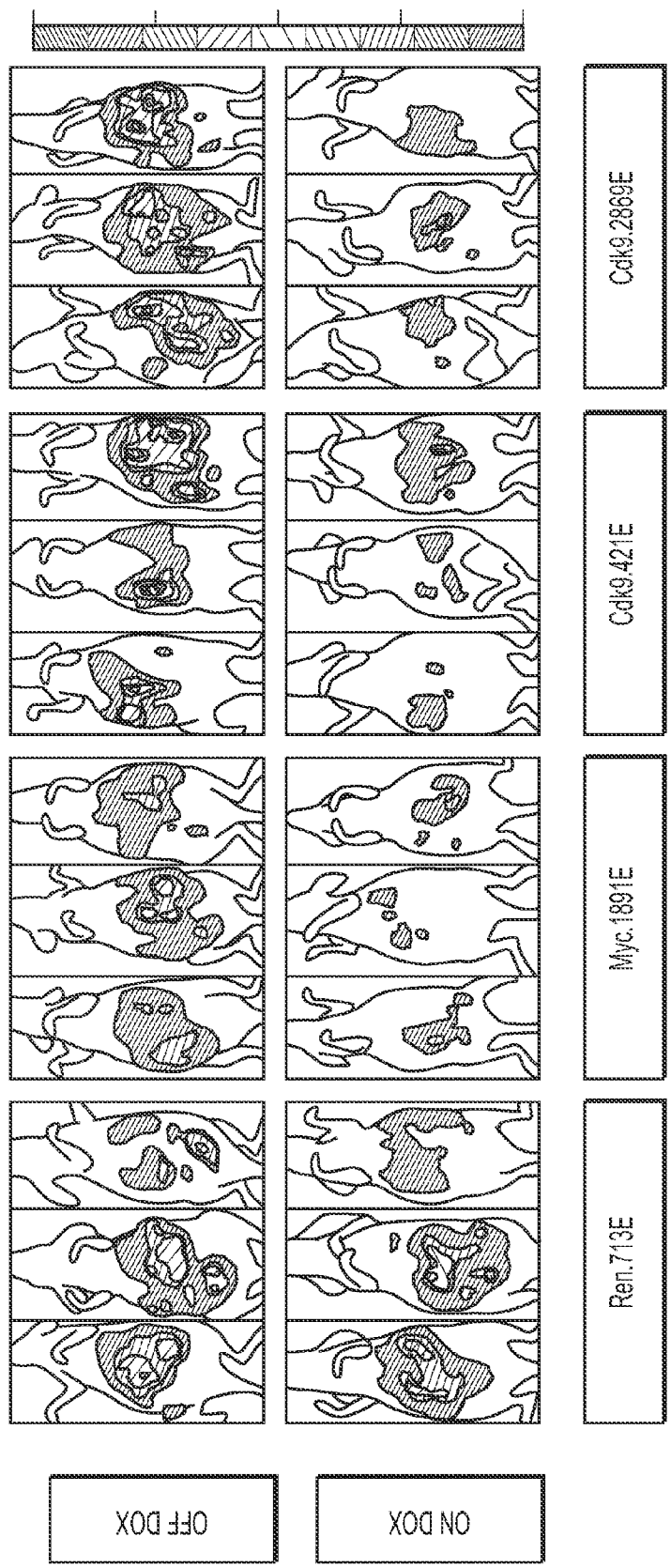
(FIG. 7D) Bioluminescent imaging of representative mice orthotopically transplanted with MP1 HCC cells harboring the indicated TRMPV-Neo-miR-E shRNAs. Doxycycline was administered upon disease onset, seven days after transplant.

RNAi-mediated Suppression of CDK9 Approximates the Effect of Myc Inhibition in Eliciting Anti-Tumor Effects in HCC In Vivo To suppress CDK9 in established tumors in mice, MP1 murine HCC cells were transduced with Luciferase and dox-inducible TRMPV-Neo-miR-E constructs containing CDK9 shRNAs or control shRNAs (Renilla and Myc), and were transplanted into the livers of recipient mice by subcapsular injection. Upon detection of a luminescent signal, the animals were randomized and treated with dox to induce shRNA expression. Tumors bearing CDK9 shRNAs exhibited a prominent decrease in the levels of Ser2 phosphorylation of RNA pol II, implying that transcription elongation was efficiently repressed (FIG. 7A). By day 8, bioluminescent imaging revealed that mice from the untreated group (no dox) displayed large hepatic tumors; however, knockdown of CDK9 or Myc led to a comparable and significant delay in tumor growth (FIGS. 7B and 7C). Ki67 staining of histological sections revealed that tumors expressing shRNAs for CDK9 or Myc showed less proliferation compared to tumors expressing the control Renilla shRNA (FIG. 7D). Therefore, RNAi-mediated suppression of CDK9 approximates the effect of Myc inhibition in eliciting anti-tumor effects in HCC in vivo.

Figures 7E, 7F:
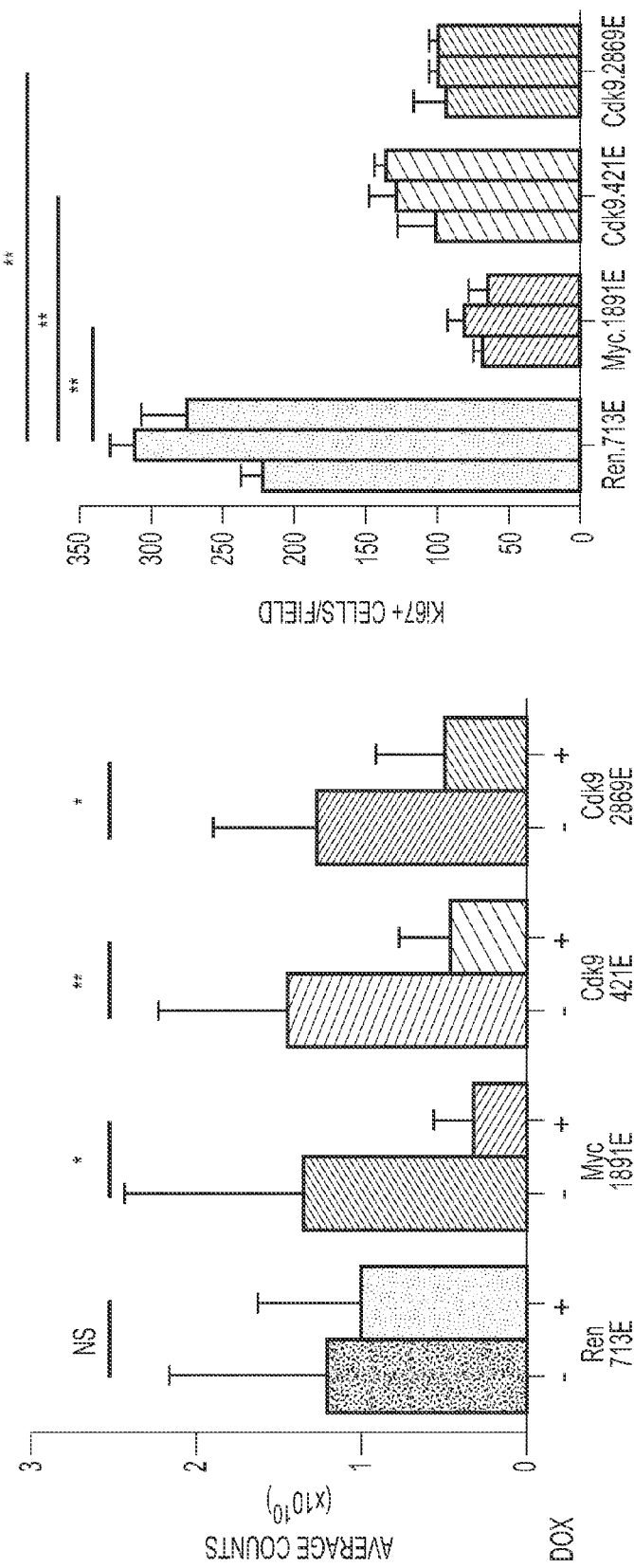
(FIG. 7E) Quantification of bioluminescent imaging responses with or without doxycycline treatment. Values are mean+SD of six independent tumors.
(FIG. 7F) Quantification of the number of Ki67 positive cells per field, after analyzing three fields per animal, and three animals per condition. Values are mean±SD.
Figure 7G:
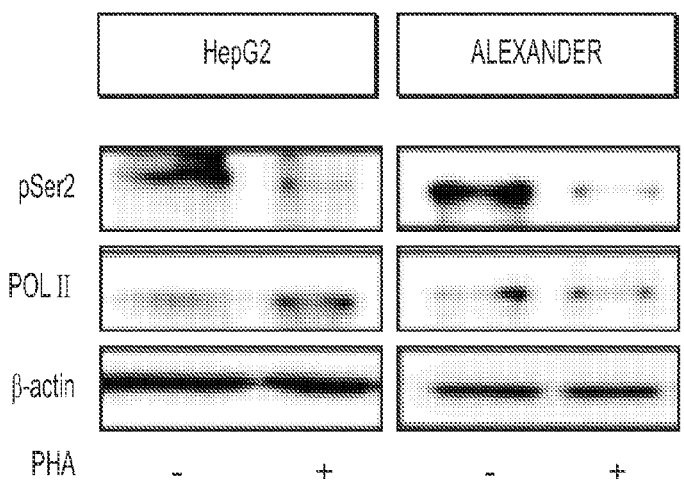
(FIG. 7G) Immunoblot showing the effects caused by PHA-767491 in two representative tumors. PHA-767491 treatment leads to a decrease in the levels of phosphorylation of Ser2 of RNA pol II (pSer2) and mild changes in total RNA pol II levels (Pol II). β-actin was used as loading control.
Figure 7H:
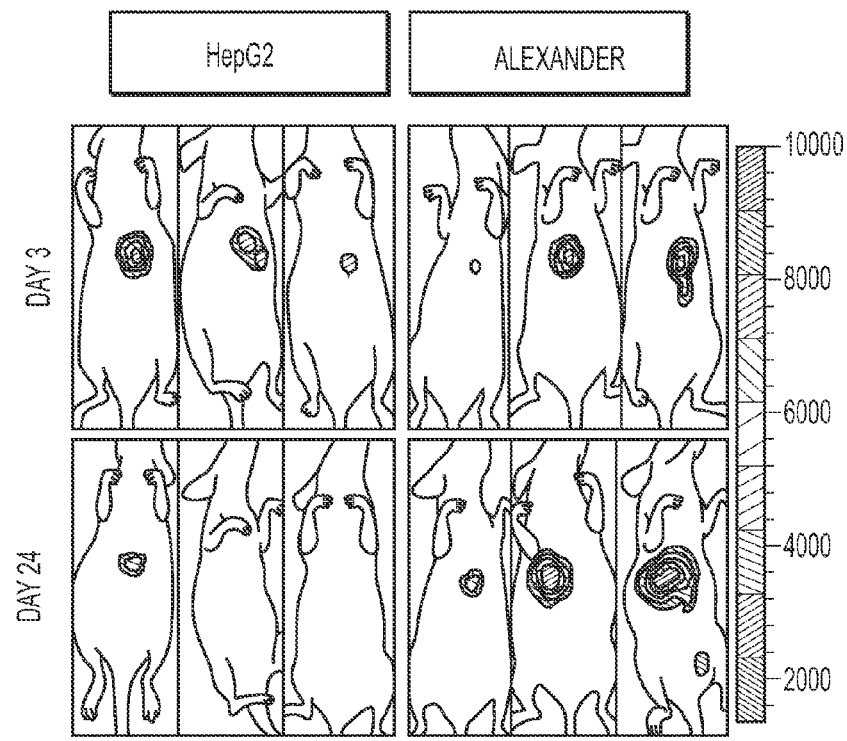
(FIG. 7H) Bioluminescent imaging of representative mice orthotopically transplanted with either HepG2 or Alexander HCC cells. PHA-767491 was administered upon disease onset (considered as day 0), 28 days after transplant. Days 3 and 24 of treatment are shown.
Figure 7J:
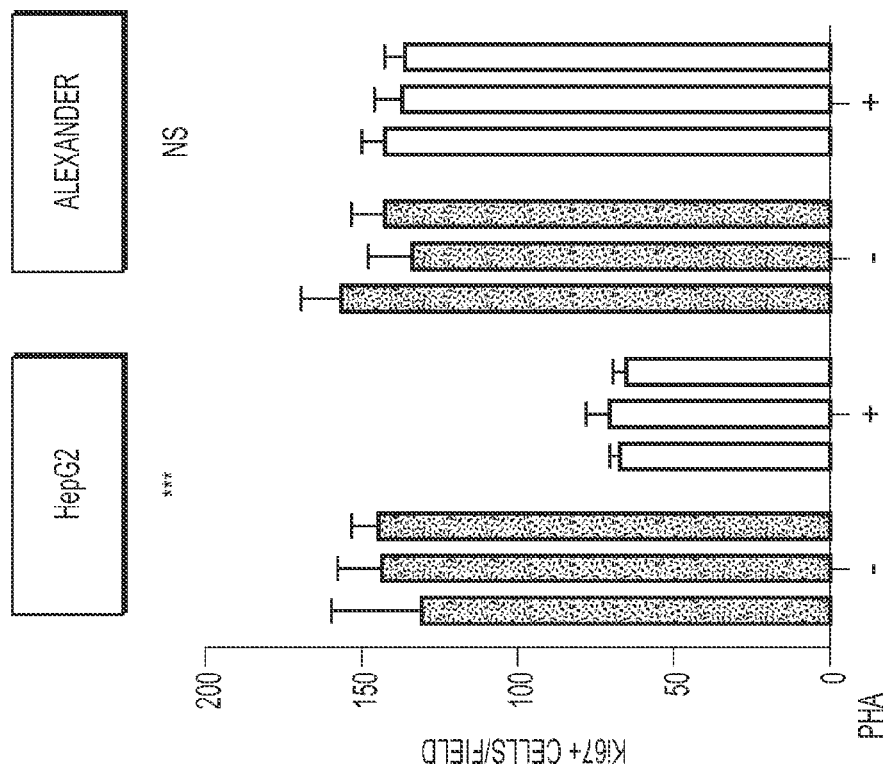
(FIG. 7J) Quantification of the number of Ki67 positive cells per field, after analyzing three fields per animal, and three animals per condition. Values are mean±SD. MP1, Myc;p53−/− murine HCC clone #1 cells; Dox, doxycycline; The "E" letter after the name of the shRNA denotes that the shRNA is cloned into miR-E backbone instead of miR-30; PHA, PHA-767491.
Figure 7I:
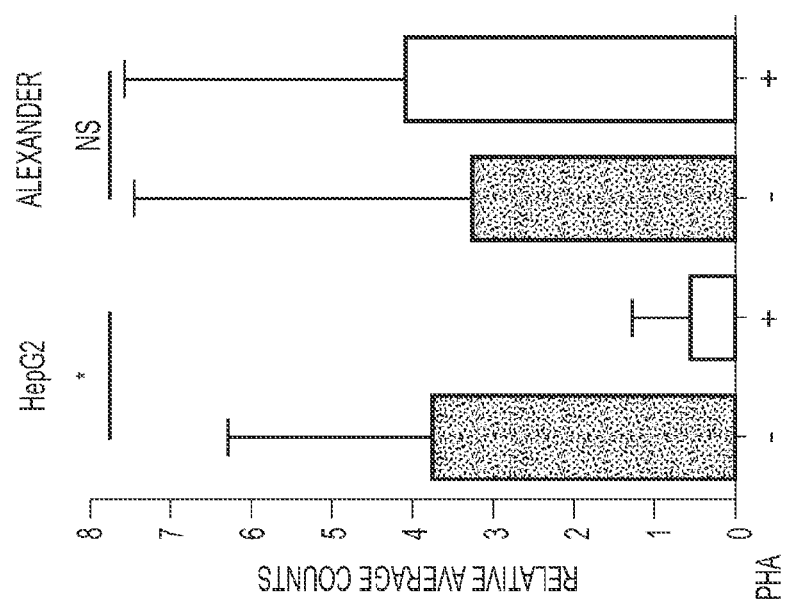
(FIG. 7I) Quantification of bioluminescent imaging responses with or without PHA-767491 treatment. Values are mean+SD of seven or eight independent tumors.
Figure 8A:
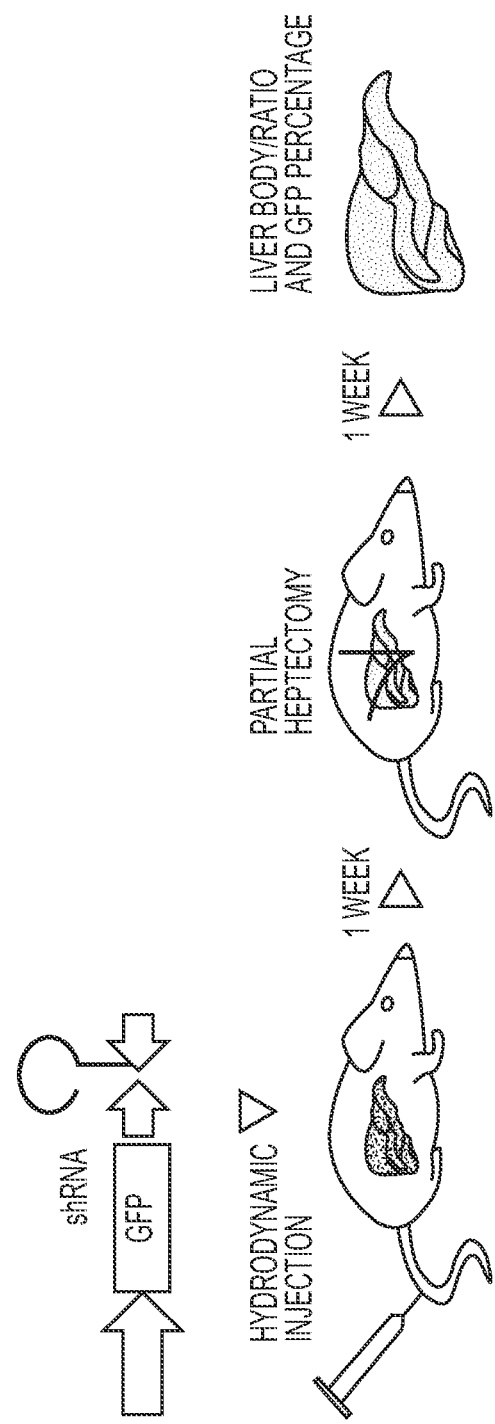
(FIG. 8A) Schematic representation of the liver regeneration. miRE shRNA transposon vectors were injected together with CMV-SB13 transposase by hydrodynamic tail vein injection. Partial hepatectomy was performed after one week. Liver/body ratio and GFP percentage were examined after two weeks.
Figure 8B:
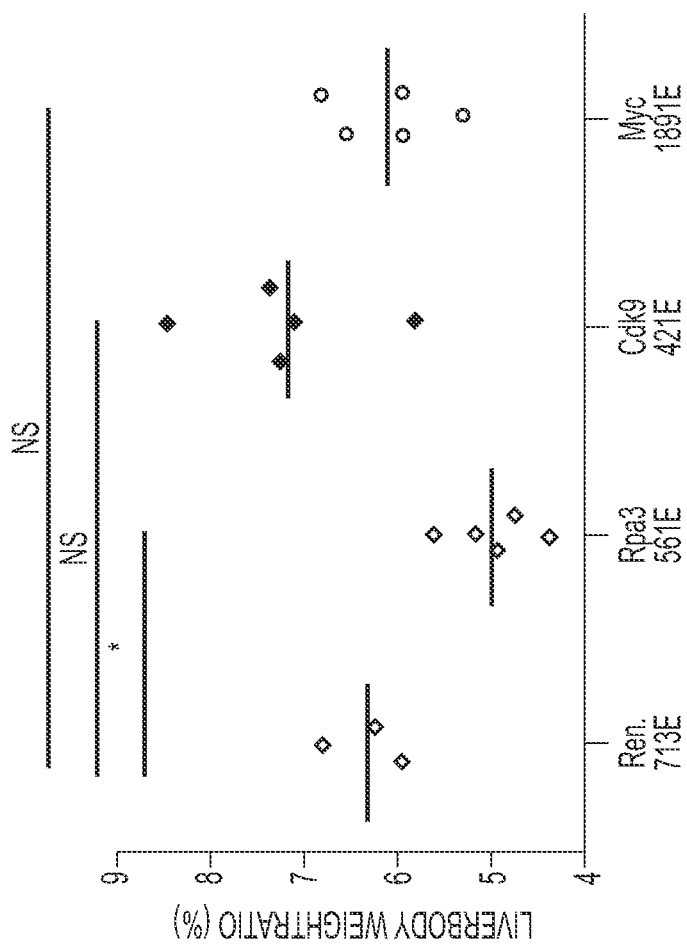
(FIG. 8B) CDK9 inhibition does not show significant impact on liver/body ratio, compared to Ren.713E (neutral control). shRpa3.561E is used as a positive control.
Figure 8C:
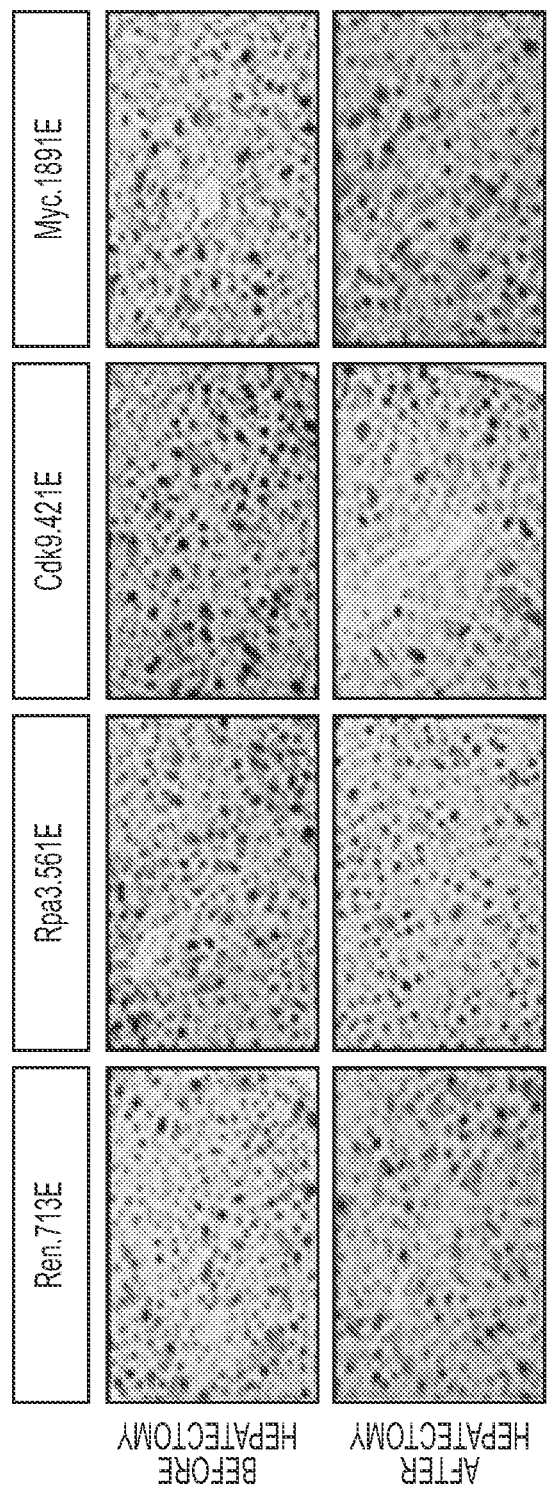
(FIG. 8C) Representative histological analysis of liver, stained for GFP.
Figure 8D:
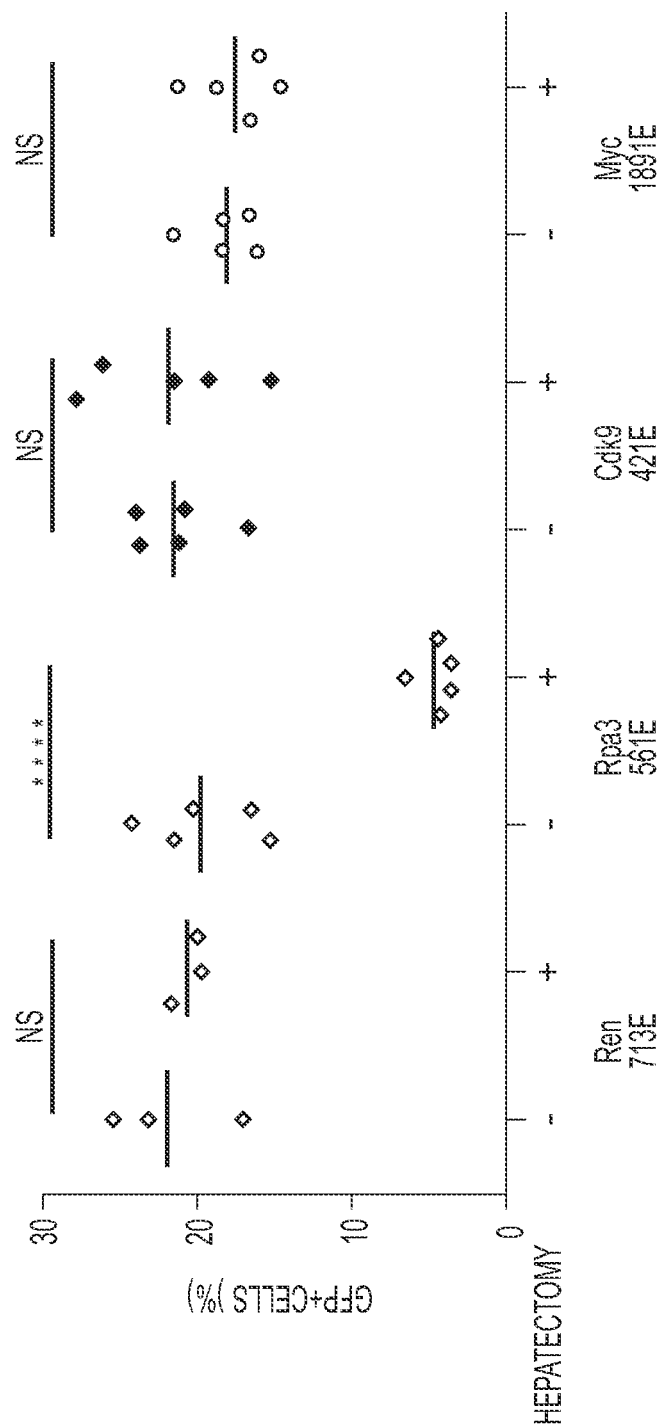
(FIG. 8D) CDK9 inhibition does not show significant impact on the percentage of GFP$^+$ cells before and after partial hepatectomy.
Figure 9A:
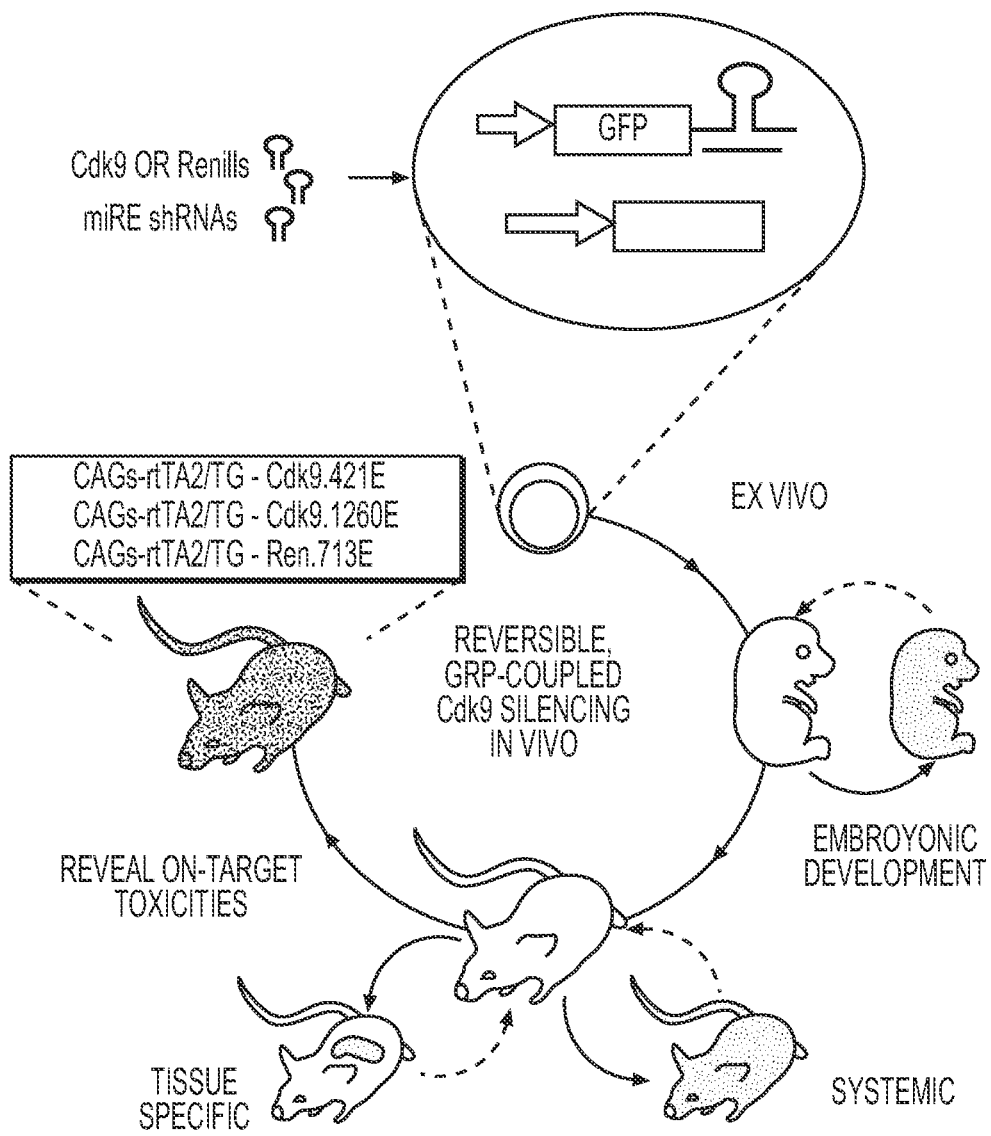
(FIG. 9A) Schematic representation of the generation and application of shRNA transgenic mice. TRE-Driven miRE shRNAs are targeted to the ColA1 locus to drive doxycycline (dox)-dependent genes knockdown in ES Cells, embryonic and adult tissues of the mouse. By using a sensitive and widely expressed rtTA mice strain, CAGs-rtTA3, GFP-miRE shRNAs can be efficiently expressed in most tissues to study on-target toxicities.
Figure 9B:
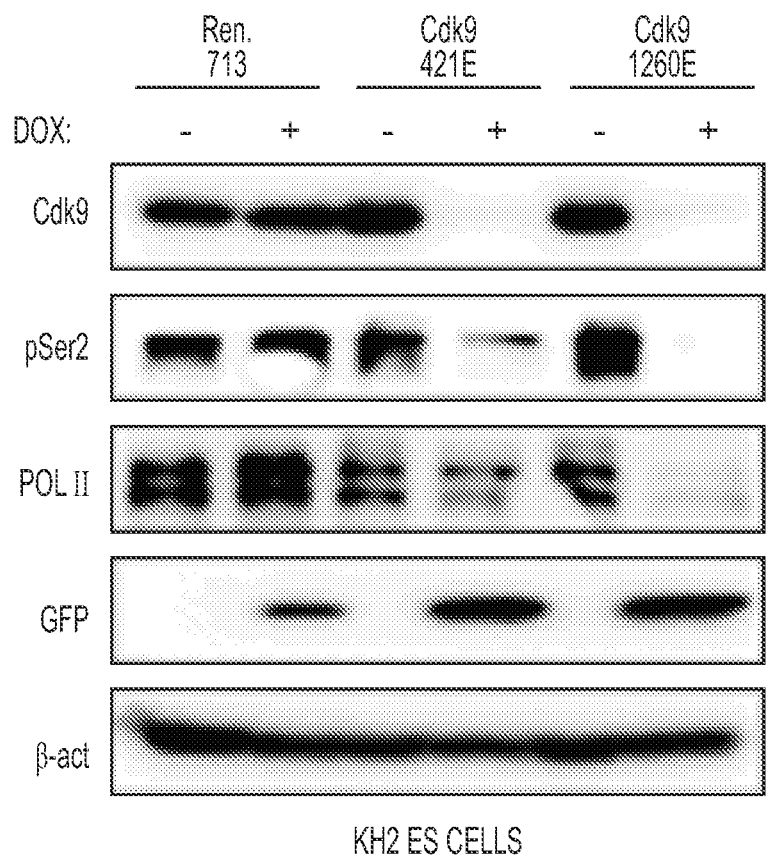
(FIG. 9B) Western blot analyses of CDK9 and RNAPII pSer2 inhibitions in dox-treated ES cell clones containing R26-rtTA and Ren.713E (neutral control) or two CDK9 miRE shRNAs (CDK9.421E and CDK9.1260E).
Figure 9C:
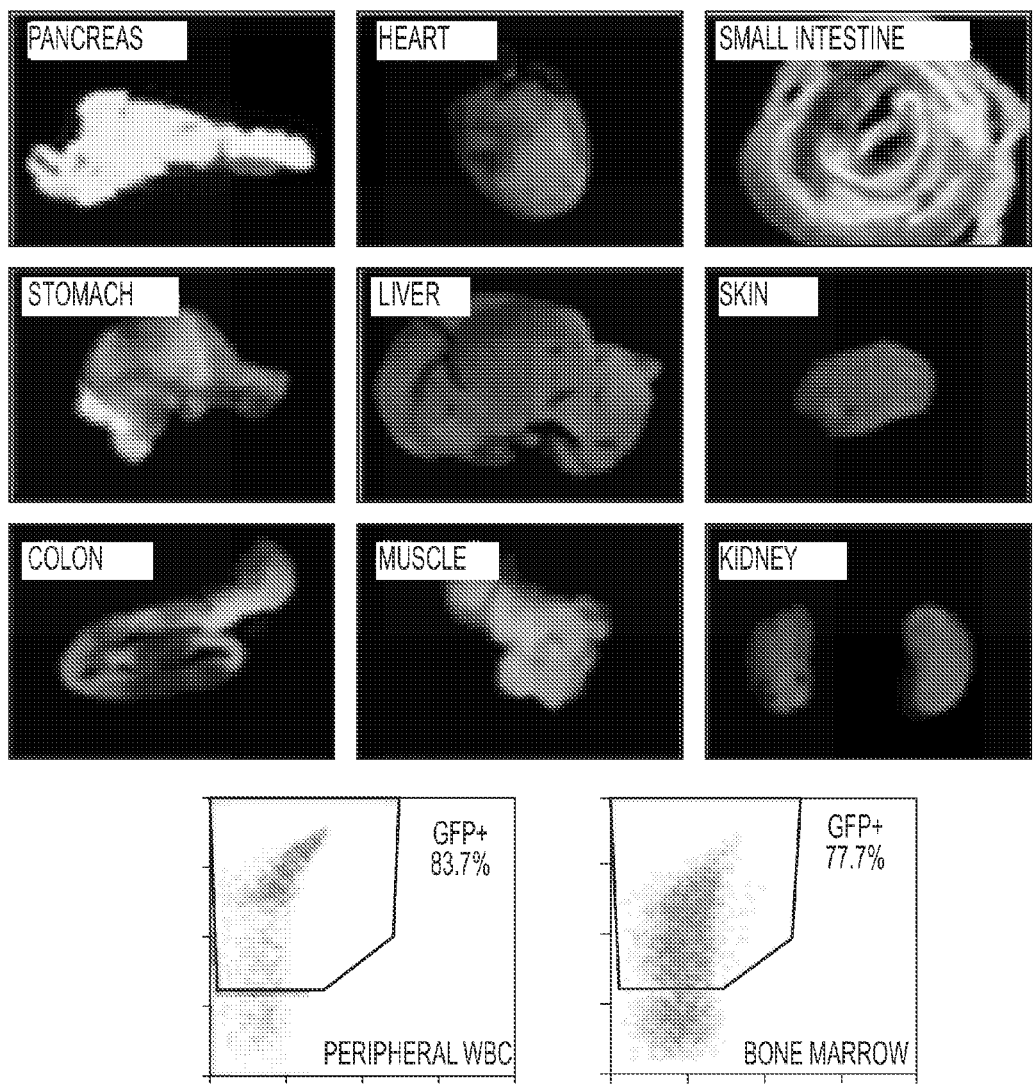
(FIG. 9C) Systematic knockdown of CDK9 and expression of GFP in most tissues from CAGs-rtTA3 expressing shRen.713E, shCDK9.421E and shCDK9.1260E, maintained on a dox diet for 2 weeks.
Figure 9D:
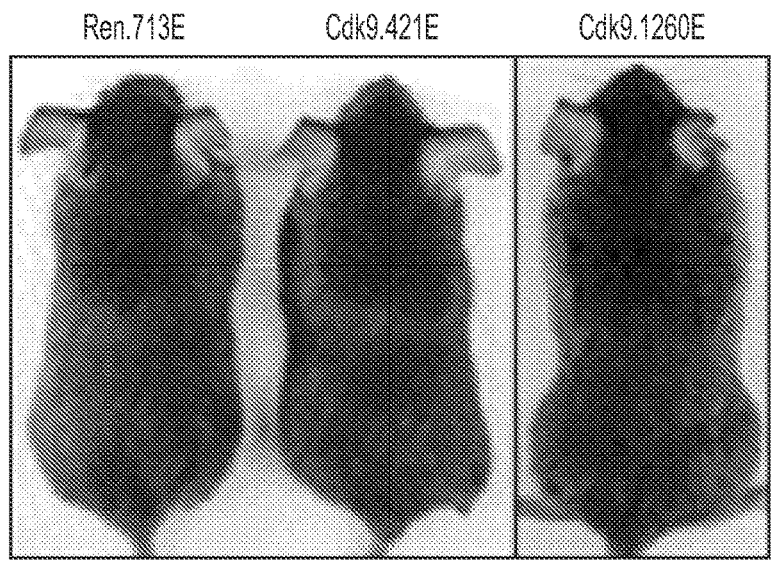
(FIG. 9D) Representative images for CAGs-rtTA3 expressing shRen.713E, shCDK9.421E and shCDK9.1260E mice after 2-week dox diet are shown. No significant difference of the appearance between the mice.
Figure 9E:
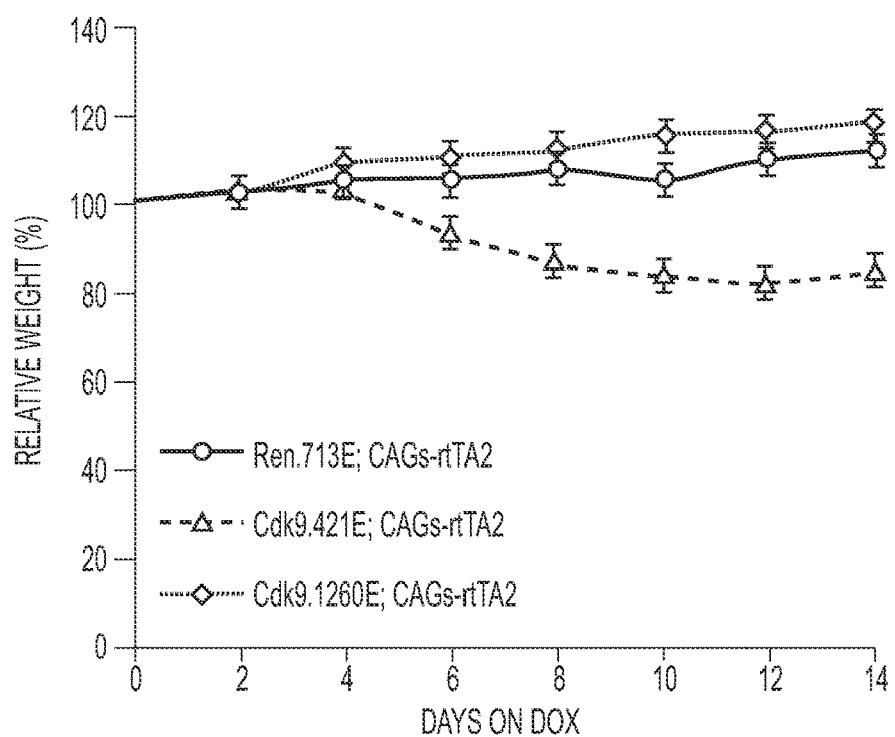
(FIG. 9E) Mean weight changes (g) of male and female (combined) CAGs-rtTA3/+; TG-Ren.713E, TG-CDK9.421E and TG-CDK9.1260E mice on the dox diet, relative to day 0 of dox treatment. Error bars represent SEM (n=3).

Growth-inhibitory effects of pharmacological CDK9 inhibition in a series of human HCC xenografts expressing luciferase were also investigated. Treatment with PHA-767491 (50 mg/kg; twice a day; 5 days per week) or vehicle was initiated upon detection of bioluminescence. Consistent with previous findings, PHA-767491 treatment was well tolerated in mice and triggered a decrease in Pol II Ser2 phosphorylation in the emerging tumors (FIG. 7E). In high MYC expressing HepG2 cells, PHA-767491 also decreased tumor-cell proliferation, which was associated with substantial inhibition of tumor growth and some tumor regressions (FIGS. 7F-7H). By marked contrast, the same treatment in low MYC expressing Alexander cells produced little if any effect, despite detectable decrease in Pol II Ser2 phosphorylation (FIGS. 7E-7H). Thus, CDK9 is required for the maintenance of MYC-overexpressing HCC, implicating transcriptional elongation as important for MYC dependency in vivo.

Example 7

Liver Regeneration to Reveal the Therapeutic Index Associated with CDK9 Inhibition In Vivo miRE shRNA transposon vectors were injected into mice together with CMV-SB13 transposase by hydrodynamic tail vein injection and partial hepatectomy was performed after one week (FIG. 8). Liver/body ratio and GFP percentage of the mice were examined after two weeks. CDK9 inhibition does not show significant impact on liver/body ratio, compared to Ren.713E (neutral control). CDK9 inhibition does not show significant impact on the percentage of GFP$^+$ cells before and after partial hepatectomy.

Example 8

Inducible and Reversible Transgenic RNAi Mice Models

TRE-Driven miRE shRNAs are targeted to the ColA1 locus to drive doxycycline (dox)-dependent genes knockdown in ES Cells, embryonic and adult tissues of the mouse (FIG. 9). No significant difference of the appearance between the mice.

What is claimed is:

1. A method of treating a patient suffering from cancer, the method comprising the steps of:
   (a) determining whether MYC is overexpressed in a biological sample from the patient; and
   (b) administering to the patient an effective amount of a CDK9 inhibitor if MYC is found to be overexpressed in the biological sample in step (a), or administering a chemotherapeutic agent that is not a CDK9 inhibitor if MYC is not found to be overexpressed in the biological sample in step (a),
   wherein the cancer is selected from the group consisting of hepatocellular carcinoma, non-small cell lung carcinoma, leukemia, and lymphoma, and
   wherein the CDK9 inhibitor is not flavopiridol.

2. The method of claim 1, further comprising the step of administering an effective amount of a second chemotherapeutic agent to the patient if overexpression of MYC is found in the biological sample.

3. The method of claim 2, wherein the second chemotherapeutic agent is a taxane, Teniposide, Gemcitabine, Dacarbazine, Flumequine, Sorafenib, Atorvastatin, tivantinib, sunitinib and Crizotinib or an anthracycline.

4. The method of claim 1, further comprising the step of subjecting the patient to radiation therapy prior to, concurrently with, or after administration of the CDK9 inhibitor.

5. The method of claim 1, further comprising the step of subjecting the patient to surgery to remove cancer cells or cancer tissue prior to, or after, administration of the CDK9 inhibitor.

6. The method of claim 1, wherein the CDK9 inhibitor is selected from the group consisting of PHA 767491, PHA-793887, PHA-848125, BAY 1143572, BAY 1112054, Cdk9 inhibitor II (CAS 140651-18-9 from Calbiochem), DRB, AZD-5438, SNS-032, dinaciclib, LY2857785, purvalanol B, CDKI-71, CDKI-73, CAN508, FIT-039, CYC065, 3,4-dimethyl-5-[2-(4-piperazin-1-yl-phenylamino)-pyrimidin-4-yl]-3H-thiazol-2-one, wogonin, apigenin, chrysin, luteolin, and 4-methyl-5-[2-(3-nitroanilino)pyrimdin-4-yl]-1,3-thiazol-2-amine.

* * * * *